(12) United States Patent
Loh et al.

(10) Patent No.: US 11,053,505 B2
(45) Date of Patent: *Jul. 6, 2021

(54) CLEAVABLE FUSION TAG FOR PROTEIN OVEREXPRESSION AND PURIFICATION

(71) Applicant: The Research Foundation for the State University of New York, Syracuse, NY (US)

(72) Inventors: Stewart N. Loh, Manlius, NY (US); Jeung-Hoi Ha, Manlius, NY (US); Adam R. Blanden, Manlius, NY (US); Alan Blayney, Syracuse, NY (US)

(73) Assignee: The Research Foundation for the State University of New York, Syracuse, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,857

(22) Filed: Feb. 11, 2019

(65) Prior Publication Data
US 2019/0161758 A1 May 30, 2019

Related U.S. Application Data

(63) Continuation of application No. 15/767,901, filed as application No. PCT/US2016/056832 on Oct. 13, 2016, now Pat. No. 10,202,607.

(60) Provisional application No. 62/240,863, filed on Oct. 13, 2015.

(51) Int. Cl.
| | |
|---|---|
| *C12N 15/62* | (2006.01) |
| *C12N 15/65* | (2006.01) |
| *C12N 15/66* | (2006.01) |
| *C07K 19/00* | (2006.01) |
| *C07K 14/245* | (2006.01) |
| *C07K 14/395* | (2006.01) |
| *C12N 15/70* | (2006.01) |
| *C12N 15/74* | (2006.01) |
| *C12N 15/79* | (2006.01) |

(52) U.S. Cl.
CPC ............ *C12N 15/62* (2013.01); *C07K 14/245* (2013.01); *C07K 14/395* (2013.01); *C07K 19/00* (2013.01); *C12N 15/65* (2013.01); *C12N 15/66* (2013.01); *C12N 15/70* (2013.01); *C12N 15/74* (2013.01); *C12N 15/79* (2013.01); *C07K 2319/00* (2013.01); *C07K 2319/10* (2013.01); *C07K 2319/50* (2013.01); *C12N 2310/3517* (2013.01); *C12N 2310/3519* (2013.01); *C12N 2510/02* (2013.01); *C12N 2810/50* (2013.01)

(58) Field of Classification Search
CPC ........ C12N 15/62; C12N 15/65; C12N 15/70; C12N 15/66
See application file for complete search history.

(56) References Cited

U.S. PATENT DOCUMENTS

| | | |
|---|---|---|
| 2004/0118681 A1 | 6/2004 | Hellinga et al. |
| 2007/0020714 A1 | 1/2007 | Lee et al. |
| 2008/0032312 A1 | 2/2008 | Amiss et al. |
| 2014/0259212 A1 | 9/2014 | Plesch et al. |

OTHER PUBLICATIONS

De Lorimier et al., Protein Science, 15, 1936-1944, 2006.*
Cuneo et al., The backbone structure of the thermophilic Thermoanaerobacter tengcongensis ribose binding protein is essentially identical to its mesophilic *E. coli* homolog, BMC Structure Biology, vol. 8, No. 20, pp. 1-11. Mar. 28, 2008.
Franco, O., et al., *Escherichia coli* SecB stimulates export without maintaining export competence of ribose-binding protein signal sequence mutants, J. Bacteriol., Oct. 1996, vol. 178, pp. 5954-5959.
Marshall, K. E., et al., FRET Imaging of Diatoms Expressing a Biosilica-Localized Ribose Sensor, PLOs One, Mar. 21, 2012, vol. 7, No. 3, e33771, pp. 1-8.
Marvin et al., Engineering Biosensors by Introducing Fluorescent Allosteric Signal Transducers: Construction of a Novel Glucose Sensor, Journal of American Chemical Society, vol. 120, No. 1, pp. 7-11. Jan. 1, 1998.
Navdaeva et al., Phosphoenolpyruvate: Sugar Phosphotransferase System from the Hyperthermophilic Thermoanaerobacter tengcongensis, Biochemistry, vol. 50, No. 7, pp. 1184-1193. Feb. 22, 2011.
International Search Report for International Patent Application No. PCT/US2016/056832, dated Jan. 10, 2017 (3 pages).

* cited by examiner

*Primary Examiner* — Maryam Monshipouri
(74) *Attorney, Agent, or Firm* — Dorsey & Whitney LLP

(57) ABSTRACT

Provided are compositions and methods for enhancing recombinant protein production. The compositions and methods involve use of Ribose Binding Protein (RBP) as a segment of a fusion polypeptide, whereby the RBP segment enhances production of the fusion protein. The fusion proteins contain the RBP sequentially in a single fusion protein with a polypeptide for which enhanced expression is desired. Recombinant expression vectors encoding the fusion proteins that contain and RBP segment are included, as are cells that contain the expression vectors. Methods for separating fusion proteins and for liberating a polypeptide segment that is part of the fusion protein are also provided.

17 Claims, 5 Drawing Sheets
Specification includes a Sequence Listing.

SEQUENCE LISTING

<160> NUMBER OF SEQ ID NOS: 17

<210> SEQ ID NO 1
<211> LENGTH: 834
<212> TYPE: DNA
<213> ORGANISM: artificial sequence
<220> FEATURE:
<223> OTHER INFORMATION: Coding for recombinant protein

<400> SEQUENCE: 1

```
atgaaagagg gcaaaacgat tggcctggtg atctctaccc tgaacaatcc gttctttgtg      60
accctgaaaa atggtgcgga agaaaaagcg aaagaactgg gttacaaaat tatcgttgaa     120
gattcgcaaa atgattcctc taaagagctg tctaatgtcg aagatttgat tcaacagaaa     180
gttgatgttc tgctgatcaa tccggtggat agcgatgcgg ttgttacggc gattaaagaa     240
gcgaatagca aaatatccc ggttattacc atcgatcgca gcgcgaatgg tggtgatgtt      300
gtttcccata tcgccagcga taatgttaag ggtggcgaaa tggccgcgga atttatcgcg     360
aaagccctga aaggcaaggg gaatgttgtg gaactggaag ggatcccggg ggcgtctgcg     420
gcacgtgatc gcggcaaagg gtttgatgaa gccattgcta agtatccgga tattaaaatc     480
gttgcaaagc aggcggcgga ttttgatcgt tccaaaggtc tgtcagtgat ggaaaacatc     540
ttgcaagccc agccgaaaat tgatgcagtg tttgcgcaaa atgatgaaat ggctctgggc     600
gctatcaaag ccattgaggc cgcgaatcgt caaggtatta ttgttgtggg ctttgatggg     660
accgaagatg ctctgaaagc gattaaagaa gggaaaatgg ctgcgaccat tgcgcagcag     720
ccggccctga tgggctcact gggtgtggag atggctgata aatacctgaa aggtgaaaaa     780
attccgaact ttattccggc agaactgaaa ctcatcacga agaaaatgt gcag            834
```

<210> SEQ ID NO 2
<211> LENGTH: 278
<212> TYPE: PRT
<213> ORGANISM: artificial sequence
<220> FEATURE:
<223> OTHER INFORMATION: modified tteRBP protein

<400> SEQUENCE: 2

```
Met Lys Glu Gly Lys Thr Ile Gly Leu Val Ile Ser Thr Leu Asn Asn
1               5                   10                  15

Pro Phe Phe Val Thr Leu Lys Asn Gly Ala Glu Glu Lys Ala Lys Glu
            20                  25                  30

Leu Gly Tyr Lys Ile Ile Val Glu Asp Ser Gln Asn Asp Ser Ser Lys
        35                  40                  45

Glu Leu Ser Asn Val Glu Asp Leu Ile Gln Gln Lys Val Asp Val Leu
    50                  55                  60

Leu Ile Asn Pro Val Asp Ser Asp Ala Val Val Thr Ala Ile Lys Glu
65                  70                  75                  80

Ala Asn Ser Lys Asn Ile Pro Val Ile Thr Ile Asp Arg Ser Ala Asn
                85                  90                  95

Gly Gly Asp Val Val Ser His Ile Ala Ser Asp Asn Val Lys Gly Gly
            100                 105                 110

Glu Met Ala Ala Glu Phe Ile Ala Lys Ala Leu Lys Gly Lys Gly Asn
        115                 120                 125

Val Val Glu Leu Glu Gly Ile Pro Gly Ala Ser Ala Ala Arg Asp Arg
    130                 135                 140

Gly Lys Gly Phe Asp Glu Ala Ile Ala Lys Tyr Pro Asp Ile Lys Ile
145                 150                 155                 160

Val Ala Lys Gln Ala Ala Asp Phe Asp Arg Ser Lys Gly Leu Ser Val
                165                 170                 175

Met Glu Asn Ile Leu Gln Ala Gln Pro Lys Ile Asp Ala Val Phe Ala
            180                 185                 190

Gln Asn Asp Glu Met Ala Leu Gly Ala Ile Lys Ala Ile Glu Ala Ala
        195                 200                 205
```

```
Asn Arg Gln Gly Ile Ile Val Val Gly Phe Asp Gly Thr Glu Asp Ala
    210                 215                 220

Leu Lys Ala Ile Lys Glu Gly Lys Met Ala Ala Thr Ile Ala Gln Gln
225                 230                 235                 240

Pro Ala Leu Met Gly Ser Leu Gly Val Glu Met Ala Asp Lys Tyr Leu
                245                 250                 255

Lys Gly Glu Lys Ile Pro Asn Phe Ile Pro Ala Glu Leu Lys Leu Ile
                260                 265                 270

Thr Lys Glu Asn Val Gln
        275

<210> SEQ ID NO 3
<211> LENGTH: 2173
<212> TYPE: DNA
<213> ORGANISM: artificial sequence
<220> FEATURE:
<223> OTHER INFORMATION: Recombinant fusion protein

<400> SEQUENCE: 3
atgggcagca gccatcacca tcatcaccac agccaggatc cgaattcgag ctcgatgaaa      60
gagggcaaaa cgattggcct ggtgatctct accctgaaca atccgttctt tgtgaccctg     120
aaaaatggtg cggaagaaaa agcgaaagaa ctgggttaca aaattatcgt tgaagattcg     180
caaaatgatt cctctaaaga gctgtctaat gtcgaagatt tgattcaaca gaaagttgat     240
gttctgctga tcaatccggt ggatagcgat gcggttgtta cggcgattaa agaagcgaat     300
agcaaaaata tcccggttta taccatcgat cgcagcgcga atggtggtga tgttgtttcc     360
catatcgcca gcgataatgt taagggtggc gaaatggccg cggaatttat cgcgaaagcc     420
ctgaaaggca aggggaatgt tgtggaactg gaaggtatcc cggggggcgtc tgcggcacgt     480 gatcgcggca aagggtttga tgaagccatt gctaagtatc cggatattaa aatcgttgca     540
aagcaggcgg cggattttga tcgttccaaa ggtctgtcag tgatggaaaa catcttgcaa     600
gcccagccga aaattgatgc agtgtttgcg caaaatgatg aaatggctct gggcgctatc     660
aaagccattg aggccgcgaa tcgtcaaggt attattgttg tgggctttga tgggaccgaa     720
gatgctctga aagcgattaa agaagggaaa atggctgcga ccattgcgca gcagccggcc     780
ctgatgggct cactgggtgt ggagatggct gataaatacc tgaaaggtga aaaaattccg     840
aactttattc cggcagaact gaaactcatc acgaaagaaa atgtgcaggg tggagcggca     900 agcggggtg ccgcgggtgg cagctctgcg gcgcgcctgc aggtcgacaa gcttgcggcc     960
gcattagaag tgctgtttca aggtccaggc atggaggagc gcagtcaga tcctagcgtc    1020 gagccccctc tgagtcagga acatttttca gacctatgga actacttcc tgaaaacaac    1080 gttctgtccc ccttgccgtc ccaagcaatg gatgatttga tgctgtcccc ggacgatatt    1140
gaacaatggt tcactgaaga cccaggtcca gatgaagctc ccagaatgcc agaggctgct    1200 cccccgtgg ccctgcacc agcagctcct acaccggcgg cccctgcacc agccccctcc    1260
tggcccctgt catcttctgt cccttcccag aaaacctacc agggcagcta cggtttccgt    1320
ctgggcttct gcattctggg acagccaag tctgtgactt gcacgtactc ccctgccctc    1380
aacaagatgt tttgccaact ggccaagacc tgccctgtgc agctgtgggt tgattccaca    1440 ccccgcccg caccgcgt cgcgccatg gccatctaca gcagtcaca gcacatgacg     1500 gaggttgtga ggcgctgccc ccaccatgag cgctgctcag atagcgatgg tctggcccct    1560
cctcagcatc ttatccgagt ggaaggaaat ttgcgtgtgg agtatttgga tgacagaaac    1620
```

-continued

```
acttttcgac atagtgtggt ggtgccctat gagccgcctg aggttggctc tgactgtacc    1680
accatccact acaactacat gtgtaacagt tcctgcatgg gcggcatgaa ccggaggccc    1740
atcctcacca tcatcacact ggaagactcc agtggtaatc tactgggacg aacagctttt    1800
gaggtgcgtg tttgtgcctg tcctgggaga gaccggcgca cagaggaaga gaatctccgc    1860
aagaaagggg agcctcacca cgagctgccc ccagggagca ctaagcgagc actgcccaac    1920
aacaccagct cctctcccca gccaaagaag aaaccactgg atggagaata tttcacccct    1980
cagatccgtg ggcgtgagcg cttcgagatg ttccgagagc tgaatgaggc cttggaactc    2040
aaggatgccc aggctgggaa ggagccaggg gggagcaggg ctcactccag ccacctgaag    2100
tccaaaaagg gtcagtctac ctcccgccat aaaaaactca tgttcaagac agaagggcct    2160
gactcagact gac                                                        2173
```

<210> SEQ ID NO 4
<211> LENGTH: 723
<212> TYPE: PRT
<213> ORGANISM: artificial sequence
<220> FEATURE:
<223> OTHER INFORMATION: Recombinant fusion protein

<400> SEQUENCE: 4

```
Met Gly Ser Ser His His His His His His Ser Gln Asp Pro Asn Ser
1               5                   10                  15

Ser Ser Met Lys Glu Gly Lys Thr Ile Gly Leu Val Ile Ser Thr Leu
            20                  25                  30

Asn Asn Pro Phe Phe Val Thr Leu Lys Asn Gly Ala Glu Glu Lys Ala
        35                  40                  45

Lys Glu Leu Gly Tyr Lys Ile Ile Val Glu Asp Ser Gln Asn Asp Ser
    50                  55                  60

Ser Lys Glu Leu Ser Asn Val Glu Asp Leu Ile Gln Gln Lys Val Asp
65                  70                  75                  80

Val Leu Leu Ile Asn Pro Val Asp Ser Asp Ala Val Val Thr Ala Ile
                85                  90                  95

Lys Glu Ala Asn Ser Lys Asn Ile Pro Val Ile Thr Ile Asp Arg Ser
            100                 105                 110

Ala Asn Gly Gly Asp Val Val Ser His Ile Ala Ser Asp Asn Val Lys
        115                 120                 125

Gly Gly Glu Met Ala Ala Glu Phe Ile Ala Lys Ala Leu Lys Gly Lys
    130                 135                 140

Gly Asn Val Val Glu Leu Glu Gly Ile Pro Gly Ala Ser Ala Ala Arg
145                 150                 155                 160

Asp Arg Gly Lys Gly Phe Asp Glu Ala Ile Ala Lys Tyr Pro Asp Ile
                165                 170                 175

Lys Ile Val Ala Lys Gln Ala Ala Asp Phe Asp Arg Ser Lys Gly Leu
            180                 185                 190

Ser Val Met Glu Asn Ile Leu Gln Ala Gln Pro Lys Ile Asp Ala Val
        195                 200                 205

Phe Ala Gln Asn Asp Glu Met Ala Leu Gly Ala Ile Lys Ala Ile Glu
    210                 215                 220

Ala Ala Asn Arg Gln Gly Ile Ile Val Val Gly Phe Asp Gly Thr Glu
225                 230                 235                 240

Asp Ala Leu Lys Ala Ile Lys Glu Gly Lys Met Ala Ala Thr Ile Ala
                245                 250                 255

Gln Gln Pro Ala Leu Met Gly Ser Leu Gly Val Glu Met Ala Asp Lys
```

```
            260                 265                 270
Tyr Leu Lys Gly Glu Lys Ile Pro Asn Phe Ile Pro Ala Glu Leu Lys
            275                 280                 285
Leu Ile Thr Lys Glu Asn Val Gln Gly Ala Ala Ser Gly Gly Ala
        290                 295                 300
Ala Gly Gly Ser Ser Ala Ala Arg Leu Gln Val Asp Lys Leu Ala Ala
305                 310                 315                 320
Ala Leu Glu Val Leu Phe Gln Gly Pro Gly Met Glu Glu Pro Gln Ser
                325                 330                 335
Asp Pro Ser Val Glu Pro Pro Leu Ser Gln Glu Thr Phe Ser Asp Leu
            340                 345                 350
Trp Lys Leu Leu Pro Glu Asn Asn Val Leu Ser Pro Leu Pro Ser Gln
        355                 360                 365
Ala Met Asp Asp Leu Met Leu Ser Pro Asp Asp Ile Glu Gln Trp Phe
    370                 375                 380
Thr Glu Asp Pro Gly Pro Asp Glu Ala Pro Arg Met Pro Glu Ala Ala
385                 390                 395                 400
Pro Pro Val Ala Pro Ala Pro Ala Ala Pro Thr Pro Ala Ala Pro Ala
                405                 410                 415
Pro Ala Pro Ser Trp Pro Leu Ser Ser Ser Val Pro Ser Gln Lys Thr
            420                 425                 430
Tyr Gln Gly Ser Tyr Gly Phe Arg Leu Gly Phe Leu His Ser Gly Thr
        435                 440                 445
Ala Lys Ser Val Thr Cys Thr Tyr Ser Pro Ala Leu Asn Lys Met Phe
    450                 455                 460
Cys Gln Leu Ala Lys Thr Cys Pro Val Gln Leu Trp Val Asp Ser Thr
465                 470                 475                 480
Pro Pro Pro Gly Thr Arg Val Arg Ala Met Ala Ile Tyr Lys Gln Ser
                485                 490                 495
Gln His Met Thr Glu Val Val Arg Arg Cys Pro His His Glu Arg Cys
            500                 505                 510
Ser Asp Ser Asp Gly Leu Ala Pro Pro Gln His Leu Ile Arg Val Glu
        515                 520                 525
Gly Asn Leu Arg Val Glu Tyr Leu Asp Asp Arg Asn Thr Phe Arg His
    530                 535                 540
Ser Val Val Val Pro Tyr Glu Pro Pro Glu Val Gly Ser Asp Cys Thr
545                 550                 555                 560
Thr Ile His Tyr Asn Tyr Met Cys Asn Ser Ser Cys Met Gly Gly Met
                565                 570                 575
Asn Arg Arg Pro Ile Leu Thr Ile Ile Thr Leu Glu Asp Ser Ser Gly
            580                 585                 590
Asn Leu Leu Gly Arg Asn Ser Phe Glu Val Arg Val Cys Ala Cys Pro
        595                 600                 605
Gly Arg Asp Arg Arg Thr Glu Glu Glu Asn Leu Arg Lys Lys Gly Glu
    610                 615                 620
Pro His His Glu Leu Pro Pro Gly Ser Thr Lys Arg Ala Leu Pro Asn
625                 630                 635                 640
Asn Thr Ser Ser Ser Pro Gln Pro Lys Lys Lys Pro Leu Asp Gly Glu
                645                 650                 655
Tyr Phe Thr Leu Gln Ile Arg Gly Arg Glu Arg Phe Glu Met Phe Arg
            660                 665                 670
Glu Leu Asn Glu Ala Leu Glu Leu Lys Asp Ala Gln Ala Gly Lys Glu
        675                 680                 685
```

Pro Gly Gly Ser Arg Ala His Ser Ser His Leu Lys Ser Lys Lys Gly
    690             695             700

Gln Ser Thr Ser Arg His Lys Lys Leu Met Phe Lys Thr Glu Gly Pro
705             710             715             720

Asp Ser Asp

<210> SEQ ID NO 5
<211> LENGTH: 1227
<212> TYPE: DNA
<213> ORGANISM: artificial sequence
<220> FEATURE:
<223> OTHER INFORMATION: Recombinant protein coding sequence

<400> SEQUENCE: 5
atgcaccatc accaccatca cctggaagtt ctgttccagg ggcccatgga ggagccgcag    60
tcagatccta gcgtcgagcc ccctctgagt caggaaacat tttcagacct atggaaacta   120
cttcctgaaa acaacgttct gtccccccttg ccgtcccaag caatggatga tttgatgctg   180
tccccggacg atattgaaca atggttcact gaagacccag gtccagatga agctcccaga   240
atgccagagc tgctcccccc cgtggcccct gcaccagcag ctcctacacc ggcggccccct   300 gcaccagccc cctcctggcc cctgtcatct tctgtcccctt cccagaaaac ctaccagggc   360
agctacggtt ccgtctgggg cttcttgcat tctgggacag ccaagtctgt gacttgcacg   420
tactcccctg ccctcaacaa gatgttttgc aactggccaa gacctgccc tgtgcagctg   480 tgggttgatt ccacaccccc gcccggcacc cgcgtccgcg ccatggccat ctacaagcag   540
tcacagcaca tgacggaggt tgtgaggcgc tgccccccacc atgagcgctg ctcagatagc   600
gatggtctgg cccctcctca gcatcttatc cgagtggaag gaaatttgcg tgtggagtat   660
ttggatgaca gaaacacttt tcgacatagt gtggtggtgc cctatgagcc gcctgaggtt   720
ggctctgact gtaccaccat ccactacaac tacatgtgta acagttcctg catgggcggc   780
atgaaccgga ggcccatcct caccatcatc acactggaag actccagtgg taatctactg   840
ggacggaaca gctttgaggt gcgtgtttgt gcctgtcctg ggagagaccg gcgcacagag   900
gaagagaatc tccgcaagaa aggggagcct caccacgagc tgcccccagg gagcactaag   960
cgagcactgc caacaacacc cagctcctct ccccagccaa agaagaaacc actggatgga   1020
gaatatttca cccttcagat ccgtgggcgt gagcgcttcg agatgttccg agagctgaat   1080
gaggccttgg aactcaagga tgcccaggct gggaaggagc caggggggag cagggctcac   1140
tccagccacc tgaagtccaa aaagggtcag tctacctccc gccataaaaa actcatgttc   1200
aagacagaag ggcctgactc agactga                                      1227

<210> SEQ ID NO 6
<211> LENGTH: 408
<212> TYPE: PRT
<213> ORGANISM: artificial sequence
<220> FEATURE:
<223> OTHER INFORMATION: Recombinant protein

<400> SEQUENCE: 6

Met His His His His His His Leu Glu Val Leu Phe Gln Gly Pro Met
1               5                   10                  15

Glu Glu Pro Gln Ser Asp Pro Ser Val Glu Pro Pro Leu Ser Gln Glu
            20                  25                  30

Thr Phe Ser Asp Leu Trp Lys Leu Leu Pro Glu Asn Asn Val Leu Ser
        35                  40                  45

Pro Leu Pro Ser Gln Ala Met Asp Asp Leu Met Leu Ser Pro Asp Asp
    50                  55                  60

Ile Glu Gln Trp Phe Thr Glu Asp Pro Gly Pro Asp Glu Ala Pro Arg
 65              70                  75                  80

Met Pro Glu Ala Ala Pro Pro Val Ala Pro Ala Pro Ala Ala Pro Thr
                85                  90                  95

Pro Ala Ala Pro Ala Pro Ala Pro Ser Trp Pro Leu Ser Ser Ser Val
                100                 105                 110

Pro Ser Gln Lys Thr Tyr Gln Gly Ser Tyr Gly Phe Arg Leu Gly Phe
            115                 120                 125

Leu His Ser Gly Thr Ala Lys Ser Val Thr Cys Thr Tyr Ser Pro Ala
        130                 135                 140

Leu Asn Lys Met Phe Cys Gln Leu Ala Lys Thr Cys Pro Val Gln Leu
145                 150                 155                 160

Trp Val Asp Ser Thr Pro Pro Gly Thr Arg Val Arg Ala Met Ala
                165                 170                 175

Ile Tyr Lys Gln Ser Gln His Met Thr Glu Val Val Arg Arg Cys Pro
                180                 185                 190

His His Glu Arg Cys Ser Asp Ser Asp Gly Leu Ala Pro Pro Gln His
            195                 200                 205

Leu Ile Arg Val Glu Gly Asn Leu Arg Val Glu Tyr Leu Asp Asp Arg
        210                 215                 220

Asn Thr Phe Arg His Ser Val Val Val Pro Tyr Glu Pro Pro Glu Val
225                 230                 235                 240

Gly Ser Asp Cys Thr Thr Ile His Tyr Asn Tyr Met Cys Asn Ser Ser
                245                 250                 255

Cys Met Gly Gly Met Asn Arg Arg Pro Ile Leu Thr Ile Ile Thr Leu
            260                 265                 270

Glu Asp Ser Ser Gly Asn Leu Leu Gly Arg Asn Ser Phe Glu Val Arg
        275                 280                 285

Val Cys Ala Cys Pro Gly Arg Asp Arg Arg Thr Glu Glu Glu Asn Leu
        290                 295                 300

Arg Lys Lys Gly Glu Pro His His Glu Leu Pro Pro Gly Ser Thr Lys
305                 310                 315                 320

Arg Ala Leu Pro Asn Asn Thr Ser Ser Ser Pro Gln Pro Lys Lys Lys
                325                 330                 335

Pro Leu Asp Gly Glu Tyr Phe Thr Leu Gln Ile Arg Gly Arg Glu Arg
            340                 345                 350

Phe Glu Met Phe Arg Glu Leu Asn Glu Ala Leu Glu Leu Lys Asp Ala
        355                 360                 365

Gln Ala Gly Lys Glu Pro Gly Gly Ser Arg Ala His Ser Ser His Leu
        370                 375                 380

Lys Ser Lys Lys Gly Gln Ser Thr Ser Arg His Lys Lys Leu Met Phe
385                 390                 395                 400

Lys Thr Glu Gly Pro Asp Ser Asp
                405

<210> SEQ ID NO 7
<211> LENGTH: 1167
<212> TYPE: DNA
<213> ORGANISM: artificial sequence
<220> FEATURE:
<223> OTHER INFORMATION: Sequence encoding recombinant fusion protein

<400> SEQUENCE: 7

-continued

```
atgtcgtact accatcacca tcaccatcac gattacgata tcccaacgac cgaaaacctg      60
tattttcagg gcgccatgga tatggtgccc atcggagccg tgcacggcgg ccatcccggc     120
gtagtgcatc cgccacagca accactgccc acggcgccca gcggcccaaa ctcgctgcag     180
ccgaactcgg tgggccagcc gggggccacc acctcctcga cagcagcgc ctccaacaag      240 agctcgctat ccgtcaagcc caactacacg ctcaagttca cgctggccgg cacaccaag      300 gcggtgtcgg cggtcaagtt cagtccgaat ggcgagtggc tggccagctc ctccgctgat     360
aaactaatca aaatctgggg agcatacgat ggcaagttcg agaagaccat tcgggccac      420 aagctgggca tcagcgatgt ggcctggagc tcagactcgc gactcctcgt gagcggcagt     480
gatgacaaga cgctcaaggt ctgggagctg agcaccggga agagcttgaa aactctgaag     540
ggccacagca actatgtgtt ctgctgcaac tttaatccgc agtccaatct gatcgtctcc     600
ggcagcttcg acgagagcgt tcgcatatgg gatgtgcgca ccggcaagtg tctgaagact     660
ctacccgccc attccgatcc cgtttcggcg gtacatttca atcgcgacgg atcgctgatc     720
gtgagcagca gctacgacgg cctctgtcgc atatgggaca cggccagtgg acagtgcttg     780
aaaaccctga tcgacgacga caatccgccc gtcagctttg taaagttctc gcccaatggc     840
aagtacattt tggccgccac gctggataat acgctcaagt tgtgggacta ctcgaagggc     900
aagtgcctga agacgtatac gggtcacaag aatgagaagt actgcatatt cgccaacttc     960
tcggtgacgg gaggaaagtg gatcgtgagt ggcagcgagg acaacatggt ctacatttgg    1020
aatctgcaga gcaaggaggt ggtgcaaaag ctgcagggac acaccgatac cgttctgtgc    1080
accgcctgcc atcccacgga gaacatcatt gcttccgcgg cgctcgagaa cgacaagacc    1140
atcaagctgt ggaagtcgga tacatag                                        1167
```

<210> SEQ ID NO 8
<211> LENGTH: 388
<212> TYPE: PRT
<213> ORGANISM: artificial sequence
<220> FEATURE:
<223> OTHER INFORMATION: Recombinant fusion protein

<400> SEQUENCE: 8

```
Met Ser Tyr Tyr His His His His His His Asp Tyr Asp Ile Pro Thr
1               5                   10                  15

Thr Glu Asn Leu Tyr Phe Gln Gly Ala Met Asp Met Val Pro Ile Gly
                20                  25                  30

Ala Val His Gly Gly His Pro Gly Val Val His Pro Pro Gln Gln Pro
            35                  40                  45

Leu Pro Thr Ala Pro Ser Gly Pro Asn Ser Leu Gln Pro Asn Ser Val
        50                  55                  60

Gly Gln Pro Gly Ala Thr Thr Ser Ser Asn Ser Ser Ala Ser Asn Lys
65                  70                  75                  80

Ser Ser Leu Ser Val Lys Pro Asn Tyr Thr Leu Lys Phe Thr Leu Ala
                85                  90                  95

Gly His Thr Lys Ala Val Ser Ala Val Lys Phe Ser Pro Asn Gly Glu
            100                 105                 110

Trp Leu Ala Ser Ser Ala Asp Lys Leu Ile Lys Ile Trp Gly Ala
        115                 120                 125

Tyr Asp Gly Lys Phe Glu Lys Thr Ile Ser Gly His Lys Leu Gly Ile
    130                 135                 140

Ser Asp Val Ala Trp Ser Ser Asp Ser Arg Leu Leu Val Ser Gly Ser
```

-continued

```
            145                 150                 155                 160
Asp Asp Lys Thr Leu Lys Val Trp Glu Leu Ser Thr Gly Lys Ser Leu
                    165                 170                 175

Lys Thr Leu Lys Gly His Ser Asn Tyr Val Phe Cys Cys Asn Phe Asn
                180                 185                 190

Pro Gln Ser Asn Leu Ile Val Ser Gly Ser Phe Asp Glu Ser Val Arg
            195                 200                 205

Ile Trp Asp Val Arg Thr Gly Lys Cys Leu Lys Thr Leu Pro Ala His
        210                 215                 220

Ser Asp Pro Val Ser Ala Val His Phe Asn Arg Asp Gly Ser Leu Ile
225                 230                 235                 240

Val Ser Ser Ser Tyr Asp Gly Leu Cys Arg Ile Trp Asp Thr Ala Ser
                245                 250                 255

Gly Gln Cys Leu Lys Thr Leu Ile Asp Asp Asn Pro Pro Val Ser
            260                 265                 270

Phe Val Lys Phe Ser Pro Asn Gly Lys Tyr Ile Leu Ala Ala Thr Leu
        275                 280                 285

Asp Asn Thr Leu Lys Leu Trp Asp Tyr Ser Lys Gly Lys Cys Leu Lys
        290                 295                 300

Thr Tyr Thr Gly His Lys Asn Glu Lys Tyr Cys Ile Phe Ala Asn Phe
305                 310                 315                 320

Ser Val Thr Gly Gly Lys Trp Ile Val Ser Gly Ser Glu Asp Asn Met
                325                 330                 335

Val Tyr Ile Trp Asn Leu Gln Ser Lys Glu Val Val Gln Lys Leu Gln
            340                 345                 350

Gly His Thr Asp Thr Val Leu Cys Thr Ala Cys His Pro Thr Glu Asn
        355                 360                 365

Ile Ile Ala Ser Ala Ala Leu Glu Asn Asp Lys Thr Ile Lys Leu Trp
        370                 375                 380

Lys Ser Asp Thr
385

<210> SEQ ID NO 9
<211> LENGTH: 2049
<212> TYPE: DNA
<213> ORGANISM: artificial sequence
<220> FEATURE:
<223> OTHER INFORMATION: DNA coding sequence of recombinant fusion
      protein

<400> SEQUENCE: 9
atgggcagca gccatcacca tcatcaccac agccaggatc cgaattcgag ctcgatgaaa      60
gagggcaaaa cgattggcct ggtgatctct accctgaaca atccgttctt tgtgaccctg     120
aaaaatggtg cggaagaaaa agcgaaagaa ctgggttaca aaattatcgt tgaagattcg     180
caaaatgatt cctctaaaga gctgtctaat gtcgaagatt tgattcaaca gaaagttgat     240
gttctgctga tcaatccggt ggatagcgat gcggttgtta cggcgattaa agaagcgaat     300
agcaaaaata tcccggttat taccatcgat cgcagcgcga atggtggtga tgttgtttcc     360
catatcgcca gcgataatgt taagggtggc gaaatggccg cggaatttat cgcgaaagcc     420
ctgaaaggca aggggaatgt tgtggaactg aaggtatcc ggggggcgtc tgcggcacgt      480
gatcgcggca agggtttga tgaagccatt gctaagtatc cggatattaa aatcgttgca     540
aagcaggcgg cggattttga tcgttccaaa ggtctgtcag tgatggaaaa catcttgcaa     600
gcccagccga aaattgatgc agtgtttgcg caaaatgatg aaatggctct gggcgctatc     660
```

```
aaagccattg aggccgcgaa tcgtcaaggt attattgttg tgggctttga tgggaccgaa    720
gatgctctga aagcgattaa agaagggaaa atggctgcga ccattgcgca gcagccggcc    780
ctgatgggct cactgggtgt ggagatggct gataaatacc tgaaaggtga aaaaattccg    840
aactttattc cggcagaact gaaactcatc acgaaagaaa atgtgcaggg tggagcggca    900
agcgggggtg ccgcgggtgg cagctctgcg gccgcattag aagtgctgtt tcaaggtcca    960
ggcatggtgc ccatcggagc cgtgcacggc ggccatcccg cgtagtgca tccgccacag     1020 caaccactgc ccacggcgcc cagcggccca aactcgctgc agccgaactc ggtgggccag    1080
ccgggggcca ccacctcctc gaacagcagc gcctccaaca gagctcgct atccgtcaag     1140 cccaactaca cgctcaagtt cacgctggcc gggcacacca aggcggtgtc ggcggtcaag    1200
ttcagtccga atggcgagtg gctggccagc tcctccgctg ataaactaat caaaatctgg    1260
ggagcatacg atggcaagtt cgagaagacc atttcgggcc acaagctggg catcagcgat    1320
gtggcctgga gctcagactc gcgactcctc gtgagcggca gtgatgacaa gacgctcaag    1380
gtctgggagc tgagcaccgg gaagagcttg aaaactctga agggccacag caactatgtg    1440
ttctgctgca actttaatcc gcagtccaat ctgatcgtct ccggcagctt cgacgagagc    1500
gttcgcatat gggatgtgcg caccggcaag tgtctgaaga ctctacccgc ccattccgat    1560
cccgtttcgg cggtacattt caatcgcgac ggatcgctga tcgtgagcag cagctacgac    1620
ggcctctgtc gcatatggga cacggccagt ggacagtgct tgaaaaccct gatcgacgac    1680
gacaatccgc ccgtcagctt tgtaaagttc tcgcccaatg gcaagtacat tttggccgcc    1740
acgctggata atacgctcaa gttgtgggac tactcgaagg gcaagtgcct gaagacgtat    1800
acgggtcaca gaatgagaa gtactgcata ttcgccaact tctcggtgac gggaggaaag    1860
tggatcgtga gtggcagcga ggacaacatg gtctacattt ggaatctgca gagcaaggag    1920
gtggtgcaaa agctgcaggg acacaccgat accgttctgt gcaccgcctg ccatcccacg    1980
gagaacatca ttgcttccgc ggcgctcgag aacgacaaga ccatcaagct gtggaagtcg    2040
gatacatag                                                           2049
```

<210> SEQ ID NO 10
<211> LENGTH: 616
<212> TYPE: PRT
<213> ORGANISM: artificial sequence
<220> FEATURE:
<223> OTHER INFORMATION: Amino acid sequence of recombinant fusion
      protein

<400> SEQUENCE: 10

```
Met Gly Ser Ser His His His His His His Ser Gln Asp Pro Asn Ser
1               5                   10                  15

Ser Ser Met Lys Glu Gly Lys Thr Ile Gly Leu Val Ile Ser Thr Leu
            20                  25                  30

Asn Asn Pro Phe Phe Val Thr Leu Lys Asn Gly Ala Glu Glu Lys Ala
        35                  40                  45

Lys Glu Leu Gly Tyr Lys Ile Ile Val Glu Asp Ser Gln Asn Asp Ser
    50                  55                  60

Ser Lys Glu Leu Ser Asn Val Glu Asp Leu Gln Gln Lys Val Asp
65                  70                  75                  80

Val Leu Leu Ile Asn Pro Val Asp Ser Asp Ala Val Val Thr Ala Ile
                85                  90                  95

Lys Glu Ala Asn Ser Lys Asn Ile Pro Val Ile Thr Ile Asp Arg Ser
```

```
                100               105               110
Ala Asn Gly Gly Asp Val Val Ser His Ile Ala Ser Asp Asn Val Lys
            115               120               125
Gly Gly Glu Met Ala Ala Glu Phe Ile Ala Lys Ala Leu Lys Gly Lys
            130               135               140
Gly Asn Val Val Glu Leu Glu Gly Ile Pro Gly Ala Ser Ala Ala Arg
145               150               155               160
Asp Arg Gly Lys Gly Phe Asp Glu Ala Ile Ala Lys Tyr Pro Asp Ile
                165               170               175
Lys Ile Val Ala Lys Gln Ala Ala Asp Phe Asp Arg Ser Lys Gly Leu
            180               185               190
Ser Val Met Glu Asn Ile Leu Gln Ala Gln Pro Lys Ile Asp Ala Val
            195               200               205
Phe Ala Gln Asn Asp Glu Met Ala Leu Gly Ala Ile Lys Ala Ile Glu
            210               215               220
Ala Ala Asn Arg Gln Gly Ile Ile Val Val Gly Phe Asp Gly Thr Glu
225               230               235               240
Asp Ala Leu Lys Ala Ile Lys Glu Gly Lys Met Ala Ala Thr Ile Ala
                245               250               255
Gln Gln Pro Ala Leu Met Gly Ser Leu Gly Val Glu Met Ala Asp Lys
            260               265               270
Tyr Leu Lys Gly Glu Lys Ile Pro Asn Phe Ile Pro Ala Glu Leu Lys
            275               280               285
Leu Ile Thr Lys Glu Asn Val Gln Gly Gly Ala Ala Ser Gly Gly Ala
            290               295               300
Ala Gly Gly Ser Ser Ala Ala Ala Leu Glu Val Leu Phe Gln Gly Pro
305               310               315               320
Gly Met Val Pro Ile Gly Ala Val His Gly His Pro Gly Val Val
                325               330               335
His Pro Pro Gln Gln Pro Leu Pro Thr Ala Pro Ser Gly Pro Asn Ser
            340               345               350
Leu Gln Pro Asn Ser Val Gly Gln Pro Gly Ala Thr Thr Ser Ser Asn
            355               360               365
Ser Ser Ala Ser Asn Lys Ser Ser Leu Ser Val Lys Pro Asn Tyr Thr
            370               375               380
Leu Lys Phe Thr Leu Ala Gly His Thr Lys Ala Val Ser Ala Val Lys
385               390               395               400
Phe Ser Pro Asn Gly Glu Trp Leu Ala Ser Ser Ala Asp Lys Leu
                405               410               415
Ile Lys Ile Trp Gly Ala Tyr Asp Gly Lys Phe Glu Lys Thr Ile Ser
            420               425               430
Gly His Lys Leu Gly Ile Ser Asp Val Ala Trp Ser Ser Asp Ser Arg
            435               440               445
Leu Leu Val Ser Gly Ser Asp Asp Lys Thr Leu Lys Val Trp Glu Leu
            450               455               460
Ser Thr Gly Lys Ser Leu Lys Thr Leu Lys Gly His Ser Asn Tyr Val
465               470               475               480
Phe Cys Cys Asn Phe Asn Pro Gln Ser Asn Leu Ile Val Ser Gly Ser
                485               490               495
Phe Asp Glu Ser Val Arg Ile Trp Asp Val Arg Thr Gly Lys Cys Leu
            500               505               510
Lys Thr Leu Pro Ala His Ser Asp Pro Val Ser Ala Val His Phe Asn
            515               520               525
```

```
Arg Asp Gly Ser Leu Ile Val Ser Ser Ser Tyr Asp Gly Leu Cys Arg
    530                 535                 540

Ile Trp Asp Thr Ala Ser Gly Gln Cys Leu Lys Thr Leu Ile Asp Asp
545                 550                 555                 560

Asp Asn Pro Pro Val Ser Phe Val Lys Phe Ser Pro Asn Gly Lys Tyr
                565                 570                 575

Ile Leu Ala Ala Thr Leu Asp Asn Thr Leu Lys Leu Trp Asp Tyr Ser
            580                 585                 590

Lys Gly Lys Cys Leu Lys Thr Tyr Ala Ala Leu Glu Asn Asp Lys Thr
    595                 600                 605

Ile Lys Leu Trp Lys Ser Asp Thr
    610                 615

<210> SEQ ID NO 11
<211> LENGTH: 2091
<212> TYPE: DNA
<213> ORGANISM: artificial sequence
<220> FEATURE:
<223> OTHER INFORMATION: DNA coding sequence for recombinant fusion
      protein

<400> SEQUENCE: 11
```

| | | | | | |
|---|---|---|---|---|---|
| atgggcagca | gccatcacca | tcatcaccac | agccaggatc | cgaattcgag ctcgatgaaa | 60 |
| gagggcaaaa | cgattggcct | ggtgatctct | accctgaaca | tccgttcttt gtgaccctg | 120 |
| aaaaatggtg | cggaagaaaa | agcgaaagaa | ctgggttaca | aaattatcgt tgaagattcg | 180 |
| caaaatgatt | cctctaaaga | gctgtctaat | gtcgaagatt | tgattcaaca gaaagttgat | 240 |
| gttctgctga | tcaatccggt | ggatagcgat | gcggttgtta | cggcgattaa agaagcgaat | 300 |
| agcaaaaata | tcccggttat | taccatcgat | cgcagcgcga | tggtggtgat gttgttttcc | 360 |
| catatcgcca | gcgataatgt | taagggtggc | gaaatggccg | cggaatttat cgcgaaagcc | 420 |
| ctgaaaggca | aggggaatgt | tgtggaactg | gaaggtatcc | cggggggcgtc tgcggcacgt | 480 |
| gatcgcggca | agggtttgat | gaagccatt | gctaagtatc | cggatattaa aatcgttgca | 540 |
| aagcaggcgg | cggattttga | tcgttccaaa | ggtctgtcag | tgatggaaaa catcttgcaa | 600 |
| gcccagccga | aaattgatgc | agtgtttgcg | caaaatgatg | aaatggctct gggcgctatc | 660 |
| aaagccattg | aggccgcgaa | tcgtcaaggt | attattgttg | tgggctttga tgggaccgaa | 720 |
| gatgctctga | aagcgattaa | agaagggaaa | atggctgcga | ccattgcgca gcagccggcc | 780 |
| ctgatgggct | cactgggtgt | ggagatggct | gataaatacc | tgaaaggtga aaaaattccg | 840 |
| aactttattc | cggcagaact | gaaactcatc | acgaaagaaa | atgtgcaggg tggagcggca | 900 |
| agcggggtg | ccgcgggtgg | cagctctgcg | gccgcattag | aagtgctgtt tcaaggtcca | 960 |
| ggcatggatt | ctgaggttgc | tgctttggtt | attgataacg | ttctggtat gtgtaaagcc | 1020 |
| ggttttgccg | gtgacgacgc | tcctcgtgct | gtcttcccat | ctatcgtcgg tagaccaaga | 1080 |
| caccaaggta | tcatggtcgg | tatgggtcaa | aaagactcct | acgttggtga tgaagctcaa | 1140 |
| tccaagagag | gtatcttgac | tttacgttac | ccaattgaac | acggtattgt caccaactgg | 1200 |
| gacgatatgg | aaaagatctg | gcatcatacc | ttctacaacg | aattgagagt tgccccagaa | 1260 |
| gaacaccctg | ttcttttgac | tgaagctcca | atgaaccctaa | atcaaacag agaaaagatg | 1320 |
| actcaaatta | tgtttgaaac | tttcaacgtt | ccagccttct | acgtttccat ccaagccgtt | 1380 |
| ttgtccttgt | actcttccgg | tagaactact | ggtattgttt | ggattccgg tgatggtgtt | 1440 |
| actcacgtcg | ttccaattta | cgctggtttc | tctctacctc | acgccatttt gagaatcgat | 1500 |

```
ttggccggta gagatttgac tgactacttg atgaagatct tgagtgaacg tggttactct   1560
ttctccacca ctgctgaaag agaaattgtc cgtgacatca aggaaaaact atgttacgtc   1620
gccttggact tcgaacaaga aatgcaaacc gctgctcaat cttcttcaat gaaaaatcc    1680 tacgaacttc cagatggtca agtcatcact attggtaacg aaagattcag agccccagaa   1740
gctttgttcc atccttctgt tttgggtttg gaatctgccg gtattgacca aactacttac   1800
aactccatca tgaagtgtga tgtcgatgtc cgtaaggaat tatacggtaa catcgttatg   1860
tccggtggta ccaccatgtt cccaggtatt gccgaaagaa tgcaaaagga aatcaccgct   1920
ttggctccat cttccatgaa ggtcaagatc attgctcctc agaaagaaa gtactccgtc    1980 tggattggtg gttctatctt ggcttctttg actaccttcc aacaaatgtg gatctcaaaa   2040
caagaatacg acgaaagtgg tccatctatc gttcaccaca agtgtttcta a            2091
```

<210> SEQ ID NO 12
<211> LENGTH: 696
<212> TYPE: PRT
<213> ORGANISM: artificial sequence
<220> FEATURE:
<223> OTHER INFORMATION: Amino acid sequence of recombinant fusion
      protein

<400> SEQUENCE: 12

```
Met Gly Ser Ser His His His His His Ser Gln Asp Pro Asn Ser
1               5                   10                  15

Ser Ser Met Lys Glu Gly Lys Thr Ile Gly Leu Val Ile Ser Thr Leu
            20                  25                  30

Asn Asn Pro Phe Phe Val Thr Leu Lys Asn Gly Ala Glu Glu Lys Ala
        35                  40                  45

Lys Glu Leu Gly Tyr Lys Ile Ile Val Glu Asp Ser Gln Asn Asp Ser
    50                  55                  60

Ser Lys Glu Leu Ser Asn Val Glu Asp Leu Ile Gln Gln Lys Val Asp
65                  70                  75                  80

Val Leu Leu Ile Asn Pro Val Asp Ser Asp Ala Val Val Thr Ala Ile
                85                  90                  95

Lys Glu Ala Asn Ser Lys Asn Ile Pro Val Ile Thr Ile Asp Arg Ser
            100                 105                 110

Ala Asn Gly Gly Asp Val Val Ser His Ile Ala Ser Asp Asn Val Lys
        115                 120                 125

Gly Gly Glu Met Ala Ala Glu Phe Ile Ala Lys Ala Leu Lys Gly Lys
    130                 135                 140

Gly Asn Val Val Glu Leu Glu Gly Ile Pro Gly Ala Ser Ala Ala Arg
145                 150                 155                 160

Asp Arg Gly Lys Gly Phe Asp Glu Ala Ile Ala Lys Tyr Pro Asp Ile
                165                 170                 175

Lys Ile Val Ala Lys Gln Ala Ala Asp Phe Asp Arg Ser Lys Gly Leu
            180                 185                 190

Ser Val Met Glu Asn Ile Leu Gln Ala Gln Pro Lys Ile Asp Ala Val
        195                 200                 205

Phe Ala Gln Asn Asp Glu Met Ala Leu Gly Ala Ile Lys Ala Ile Glu
    210                 215                 220

Ala Ala Asn Arg Gln Gly Ile Ile Val Val Gly Phe Asp Gly Thr Glu
225                 230                 235                 240

Asp Ala Leu Lys Ala Ile Lys Glu Gly Lys Met Ala Ala Thr Ile Ala
                245                 250                 255
```

```
Gln Gln Pro Ala Leu Met Gly Ser Leu Gly Val Glu Met Ala Asp Lys
        260                 265                 270

Tyr Leu Lys Gly Glu Lys Ile Pro Asn Phe Ile Pro Ala Glu Leu Lys
            275                 280                 285

Leu Ile Thr Lys Glu Asn Val Gln Gly Gly Ala Ala Ser Gly Gly Ala
        290                 295                 300

Ala Gly Gly Ser Ser Ala Ala Ala Leu Glu Val Leu Phe Gln Gly Pro
305                 310                 315                 320

Gly Met Asp Ser Glu Val Ala Ala Leu Val Ile Asp Asn Gly Ser Gly
                325                 330                 335

Met Cys Lys Ala Gly Phe Ala Gly Asp Asp Ala Pro Arg Ala Val Phe
                340                 345                 350

Pro Ser Ile Val Gly Arg Pro Arg His Gln Gly Ile Met Val Gly Met
            355                 360                 365

Gly Gln Lys Asp Ser Tyr Val Gly Asp Glu Ala Gln Ser Lys Arg Gly
        370                 375                 380

Ile Leu Thr Leu Arg Tyr Pro Ile Glu His Gly Ile Val Thr Asn Trp
385                 390                 395                 400

Asp Asp Met Glu Lys Ile Trp His His Thr Phe Tyr Asn Glu Leu Arg
                405                 410                 415

Val Ala Pro Glu Glu His Pro Val Leu Leu Thr Glu Ala Pro Met Asn
            420                 425                 430

Pro Lys Ser Asn Arg Glu Lys Met Thr Gln Ile Met Phe Glu Thr Phe
        435                 440                 445

Asn Val Pro Ala Phe Tyr Val Ser Ile Gln Ala Val Leu Ser Leu Tyr
    450                 455                 460

Ser Ser Gly Arg Thr Thr Gly Ile Val Leu Asp Ser Gly Asp Gly Val
465                 470                 475                 480

Thr His Val Val Pro Ile Tyr Ala Gly Phe Ser Leu Pro His Ala Ile
                485                 490                 495

Leu Arg Ile Asp Leu Ala Gly Arg Asp Leu Thr Asp Tyr Leu Met Lys
            500                 505                 510

Ile Leu Ser Glu Arg Gly Tyr Ser Phe Ser Thr Thr Ala Glu Arg Glu
        515                 520                 525

Ile Val Arg Asp Ile Lys Glu Lys Leu Cys Tyr Val Ala Leu Asp Phe
    530                 535                 540

Glu Gln Glu Met Gln Thr Ala Ala Gln Ser Ser Ser Ile Glu Lys Ser
545                 550                 555                 560

Tyr Glu Leu Pro Asp Gly Gln Val Ile Thr Ile Gly Asn Glu Arg Phe
                565                 570                 575

Arg Ala Pro Glu Ala Leu Phe His Pro Ser Val Leu Gly Leu Glu Ser
            580                 585                 590

Ala Gly Ile Asp Gln Thr Thr Tyr Asn Ser Ile Met Lys Cys Asp Val
        595                 600                 605

Asp Val Arg Lys Glu Leu Tyr Gly Asn Ile Val Met Ser Gly Gly Thr
    610                 615                 620

Thr Met Phe Pro Gly Ile Ala Glu Arg Met Gln Lys Glu Ile Thr Ala
625                 630                 635                 640

Leu Ala Pro Ser Ser Met Lys Val Lys Ile Ile Ala Pro Pro Glu Arg
                645                 650                 655

Lys Tyr Ser Val Trp Ile Gly Gly Ser Ile Leu Ala Ser Leu Thr Thr
            660                 665                 670
```

```
Phe Gln Gln Met Trp Ile Ser Lys Gln Glu Tyr Asp Glu Ser Gly Pro
            675                 680                 685

Ser Ile Val His His Lys Cys Phe
    690                 695

<210> SEQ ID NO 13
<211> LENGTH: 495
<212> TYPE: PRT
<213> ORGANISM: artificial sequence
<220> FEATURE:
<223> OTHER INFORMATION: Amino acid sequence of recombinant fusion
      protein

<400> SEQUENCE: 13

Met Gly Ser Ser His His His His His Ser Gln Asp Pro Asn Ser
1               5                   10                  15

Ser Ser Met Lys Glu Gly Lys Thr Ile Gly Leu Val Ile Ser Thr Leu
            20                  25                  30

Asn Asn Pro Phe Phe Val Thr Leu Lys Asn Gly Ala Glu Glu Lys Ala
            35                  40                  45

Lys Glu Leu Gly Tyr Lys Ile Ile Val Glu Asp Ser Gln Asn Asp Ser
    50                  55                  60

Ser Lys Glu Leu Ser Asn Val Glu Asp Leu Ile Gln Gln Lys Val Asp
65                  70                  75                  80

Val Leu Leu Ile Asn Pro Val Asp Ser Asp Ala Val Val Thr Ala Ile
                85                  90                  95

Lys Glu Ala Asn Ser Lys Asn Ile Pro Val Ile Thr Ile Asp Arg Ser
            100                 105                 110

Ala Asn Gly Gly Asp Val Val Ser His Ile Ala Ser Asp Asn Val Lys
        115                 120                 125

Gly Gly Glu Met Ala Ala Glu Phe Ile Ala Lys Ala Leu Lys Gly Lys
    130                 135                 140

Gly Asn Val Val Glu Leu Glu Gly Ile Pro Gly Ala Ser Ala Ala Arg
145                 150                 155                 160

Asp Arg Gly Lys Gly Phe Asp Glu Ala Ile Ala Lys Tyr Pro Asp Ile
                165                 170                 175

Lys Ile Val Ala Lys Gln Ala Ala Asp Phe Asp Arg Ser Lys Gly Leu
            180                 185                 190

Ser Val Met Glu Asn Ile Leu Gln Ala Gln Pro Lys Ile Asp Ala Val
        195                 200                 205

Phe Ala Gln Asn Asp Glu Met Ala Leu Gly Ala Ile Lys Ala Ile Glu
    210                 215                 220

Ala Ala Asn Arg Gln Gly Ile Ile Val Val Gly Phe Asp Gly Thr Glu
225                 230                 235                 240

Asp Ala Leu Lys Ala Ile Lys Glu Gly Lys Met Ala Ala Thr Ile Ala
                245                 250                 255

Gln Gln Pro Ala Leu Met Gly Ser Leu Gly Val Glu Met Ala Asp Lys
            260                 265                 270

Tyr Leu Lys Gly Glu Lys Ile Pro Asn Phe Ile Pro Ala Glu Leu Lys
        275                 280                 285

Leu Ile Thr Lys Glu Asn Val Gln Gly Gly Ala Ala Ser Gly Gly Ala
    290                 295                 300

Ala Gly Gly Ser Ser Ala Ala Ala Gly Gly Pro Asn Thr Glu Phe Ala
305                 310                 315                 320

Leu Ser Leu Leu Arg Lys Asn Ile Met Thr Ile Thr Thr Ser Lys Gly
                325                 330                 335
```

Glu Phe Thr Gly Leu Gly Ile His Asp Arg Val Cys Val Ile Pro Thr
                340                 345                 350

His Ala Gln Pro Gly Asp Asp Val Leu Val Asn Gly Gln Lys Ile Arg
            355                 360                 365

Val Lys Asp Lys Tyr Lys Leu Val Asp Pro Glu Asn Ile Asn Leu Glu
370                 375                 380

Leu Thr Val Leu Thr Leu Asp Arg Asn Glu Lys Phe Arg Asp Ile Arg
385                 390                 395                 400

Gly Phe Ile Ser Glu Asp Leu Glu Gly Val Asp Ala Thr Leu Val Val
                405                 410                 415

His Ser Asn Asn Phe Thr Asn Thr Ile Leu Glu Val Gly Pro Val Thr
            420                 425                 430

Met Ala Gly Leu Ile Asn Leu Ser Ser Thr Pro Thr Asn Arg Met Ile
        435                 440                 445

Arg Tyr Asp Tyr Ala Thr Lys Thr Gly Gln Cys Gly Gly Val Leu Cys
    450                 455                 460

Ala Thr Gly Lys Ile Phe Gly Ile His Val Gly Gly Asn Gly Arg Gln
465                 470                 475                 480

Gly Phe Ser Ala Gln Leu Lys Lys Gln Tyr Phe Val Glu Lys Gln
                485                 490                 495

<210> SEQ ID NO 14
<211> LENGTH: 1488
<212> TYPE: DNA
<213> ORGANISM: artificial sequence
<220> FEATURE:
<223> OTHER INFORMATION: DNA coding sequence for recombinant fusion
      protein

<400> SEQUENCE: 14
atgggcagca gccatcacca tcatcaccac agccaggatc cgaattcgag ctcgatgaaa       60
gagggcaaaa cgattggcct ggtgatctct accctgaaca atccgttctt tgtgaccctg     120
aaaaatggtg cggaagaaaa agcgaaagaa ctgggttaca aaattatcgt tgaagattcg     180
caaaatgatt cctctaaaga gctgtctaat gtcgaagatt tgattcaaca gaaagttgat     240
gttctgctga tcaatccggt ggatagcgat gcggttgtta cggcgattaa agaagcgaat     300
agcaaaaata tcccggttat taccatcgat cgcagcgcga atggtggtga tgttgtttcc     360
catatcgcca gcgataatgt taagggtggc gaaatggccg cggaatttat cgcgaaagcc     420
ctgaaaggca aggggaatgt tgtggaactg gaaggtatcc cggggcgtc tgcggcacgt     480 gatcgcggca agggtttga tgaagccatt gctaagtatc cggatattaa aatcgttgca     540
aagcaggcgg cggattttga tcgttccaaa ggtctgtcag tgatggaaaa catcttgcaa     600
gcccagccga aaattgatgc agtgtttgcg caaaatgatg aaatggctct gggcgctatc     660
aaagccattg aggccgcgaa tcgtcaaggt attattgttg tgggctttga tgggaccgaa     720
gatgctctga aagcgattaa agaagggaaa atggctgcga ccattgcgca gcagccggcc     780
ctgatgggct cactgggtgt ggagatggct gataaatacc tgaaaggtga aaaaattccg     840
aactttattc cggcagaact gaaactcatc acgaaagaaa atgtgcaggg tggagcggca     900 agcggggtg ccgcgggtgg cagctctgcg gccgcaggcg gaccaaacac agaatttgca     960
ctatccctgt taaggaaaaa cataatgact ataacaacct caagggaga gttcacaggg    1020 ttaggcatac atgatcgtgt ctgtgtgata cccacacacg cacagccctgg tgatgatgta    1080 ctagtgaatg gtcagaaaat tagagttaag gataagtaca aattagtaga tccagagaac    1140

```
attaatctag agcttacagt gttgacttta gatagaaatg aaaaattcag agatatcagg    1200
ggatttatat cagaagatct agaaggtgtg gatgccactt tggtagtaca ttcaaataac    1260
tttaccaaca ctatcttaga agttggccct gtaacaatgg caggacttat taatttgagt    1320
agcaccccca ctaacagaat gattcgttat gattatgcaa caaaaactgg gcagtgtgga    1380
ggtgtgctgt gtgctactgg taagatcttt ggtattcatg ttggcggtaa tggaagacaa    1440
ggattttcag ctcaacttaa aaacaatat tttgtagaga aacaataa                 1488
```

<210> SEQ ID NO 15
<211> LENGTH: 821
<212> TYPE: PRT
<213> ORGANISM: artificial sequence
<220> FEATURE:
<223> OTHER INFORMATION: Recombinant fusion protein

<400> SEQUENCE: 15

```
Met Gly Ser Ser His His His His His His Ser Gln Asp Pro Asn Ser
1               5                   10                  15

Ser Ser Met Lys Glu Gly Lys Thr Ile Gly Leu Val Ile Ser Thr Leu
            20                  25                  30

Asn Asn Pro Phe Phe Val Thr Leu Lys Asn Gly Ala Glu Glu Lys Ala
        35                  40                  45

Lys Glu Leu Gly Tyr Lys Ile Ile Val Glu Asp Ser Gln Asn Asp Ser
    50                  55                  60

Ser Lys Glu Leu Ser Asn Val Glu Asp Leu Ile Gln Gln Lys Val Asp
65                  70                  75                  80

Val Leu Leu Ile Asn Pro Val Asp Ser Asp Ala Val Val Thr Ala Ile
                85                  90                  95

Lys Glu Ala Asn Ser Lys Asn Ile Pro Val Ile Thr Ile Asp Arg Ser
            100                 105                 110

Ala Asn Gly Gly Asp Val Val Ser His Ile Ala Ser Asp Asn Val Lys
        115                 120                 125

Gly Gly Glu Met Ala Ala Glu Phe Ile Ala Lys Ala Leu Lys Gly Lys
    130                 135                 140

Gly Asn Val Val Glu Leu Glu Gly Ile Pro Gly Ala Ser Ala Ala Arg
145                 150                 155                 160

Asp Arg Gly Lys Gly Phe Asp Glu Ala Ile Ala Lys Tyr Pro Asp Ile
                165                 170                 175

Lys Ile Val Ala Lys Gln Ala Ala Asp Phe Asp Arg Ser Lys Gly Leu
            180                 185                 190

Ser Val Met Glu Asn Ile Leu Gln Ala Gln Pro Lys Ile Asp Ala Val
        195                 200                 205

Phe Ala Gln Asn Asp Glu Met Ala Leu Gly Ala Ile Lys Ala Ile Glu
    210                 215                 220

Ala Ala Asn Arg Gln Gly Ile Ile Val Val Gly Phe Asp Gly Thr Glu
225                 230                 235                 240

Asp Ala Leu Lys Ala Ile Lys Glu Gly Lys Met Ala Ala Thr Ile Ala
                245                 250                 255

Gln Gln Pro Ala Leu Met Gly Ser Leu Gly Val Glu Met Ala Asp Lys
            260                 265                 270

Tyr Leu Lys Gly Glu Lys Ile Pro Asn Phe Ile Pro Ala Glu Leu Lys
        275                 280                 285

Leu Ile Thr Lys Glu Asn Val Gln Gly Gly Ala Ala Ser Gly Gly Ala
    290                 295                 300
```

```
Ala Gly Gly Ser Ser Ala Ala Arg Leu Gln Val Asp Lys Leu Ala Ala
305                 310                 315                 320

Ala Leu Glu Val Leu Phe Gln Gly Pro Gly Met Cys Asn Thr Asn Met
            325                 330                 335

Ser Val Pro Thr Asp Gly Ala Val Thr Thr Ser Gln Ile Pro Ala Ser
        340                 345                 350

Glu Gln Glu Thr Leu Val Arg Pro Lys Pro Leu Leu Leu Lys Leu Leu
    355                 360                 365

Lys Ser Val Gly Ala Gln Lys Asp Thr Tyr Thr Met Lys Glu Val Leu
370                 375                 380

Phe Tyr Leu Gly Gln Tyr Ile Met Thr Lys Arg Leu Tyr Asp Glu Lys
385                 390                 395                 400

Gln Gln His Ile Val Tyr Cys Ser Asn Asp Leu Leu Gly Asp Leu Phe
            405                 410                 415

Gly Val Pro Ser Phe Ser Val Lys Glu His Arg Lys Ile Tyr Thr Met
        420                 425                 430

Ile Tyr Arg Asn Leu Val Val Asn Gln Gln Glu Ser Ser Asp Ser
    435                 440                 445

Gly Thr Ser Val Ser Glu Asn Arg Cys His Leu Glu Gly Gly Ser Asp
    450                 455                 460

Gln Lys Asp Leu Val Gln Glu Leu Gln Glu Lys Pro Ser Ser Ser
465                 470                 475                 480

His Leu Val Ser Arg Pro Ser Thr Ser Ser Arg Arg Arg Ala Ile Ser
            485                 490                 495

Glu Thr Glu Glu Asn Ser Asp Glu Leu Ser Gly Glu Arg Gln Arg Lys
        500                 505                 510

Arg His Lys Ser Asp Ser Ile Ser Leu Ser Phe Asp Glu Ser Leu Ala
    515                 520                 525

Leu Cys Val Ile Arg Glu Ile Cys Cys Glu Arg Ser Ser Ser Ser Glu
    530                 535                 540

Ser Thr Gly Thr Pro Ser Asn Pro Asp Leu Asp Ala Gly Val Ser Glu
545                 550                 555                 560

His Ser Gly Asp Trp Leu Asp Gln Asp Ser Val Ser Asp Gln Phe Ser
            565                 570                 575

Val Glu Phe Glu Val Glu Ser Leu Asp Ser Glu Asp Tyr Ser Leu Ser
        580                 585                 590

Glu Glu Gly Gln Glu Leu Ser Asp Glu Asp Asp Glu Val Tyr Gln Val
    595                 600                 605

Thr Val Tyr Gln Ala Gly Glu Ser Asp Thr Asp Ser Phe Glu Glu Asp
    610                 615                 620

Pro Glu Ile Ser Leu Ala Asp Tyr Trp Lys Cys Thr Ser Cys Asn Glu
625                 630                 635                 640

Met Asn Pro Pro Leu Pro Ser His Cys Asn Arg Cys Trp Ala Leu Arg
            645                 650                 655

Glu Asn Trp Leu Pro Glu Asp Lys Gly Lys Asp Lys Gly Glu Ile Ser
        660                 665                 670

Glu Lys Ala Lys Leu Glu Asn Ser Thr Gln Ala Glu Glu Gly Phe Asp
    675                 680                 685

Val Pro Asp Cys Lys Lys Thr Ile Val Asn Asp Ser Arg Glu Ser Cys
    690                 695                 700

Val Glu Glu Asn Asp Asp Lys Ile Thr Gln Ala Ser Gln Ser Gln Glu
705                 710                 715                 720
```

```
Ser Glu Asp Tyr Ser Gln Pro Ser Thr Ser Ser Ile Ile Tyr Ser
                725                 730                 735
Ser Gln Glu Asp Val Lys Glu Phe Glu Arg Glu Thr Gln Asp Lys
            740                 745                 750
Glu Glu Ser Val Glu Ser Ser Leu Pro Leu Asn Ala Ile Glu Pro Cys
        755                 760                 765
Val Ile Cys Gln Gly Arg Pro Lys Asn Gly Cys Ile Val His Gly Lys
    770                 775                 780
Thr Gly His Leu Met Ala Cys Phe Thr Cys Ala Lys Lys Leu Lys Lys
785                 790                 795                 800
Arg Asn Lys Pro Cys Pro Val Cys Arg Gln Pro Ile Gln Met Ile Val
                805                 810                 815
Leu Thr Tyr Phe Pro
            820

<210> SEQ ID NO 16
<211> LENGTH: 2539
<212> TYPE: DNA
<213> ORGANISM: artificial sequence
<220> FEATURE:
<223> OTHER INFORMATION: DNA sequence encoding recombinant fusion
      protein

<400> SEQUENCE: 16
ccatgggcag cagccatcac catcatcacc acagccagga tccgaattcg agctcgatga      60
aagagggcaa acgattggc ctggtgatct ctaccctgaa caatccgttc tttgtgaccc      120
tgaaaaatgg tgcggaagaa aaagcgaaag aactgggtta caaattatc gttgaagatt      180 cgcaaaatga ttcctctaaa gagctgtcta atgtcgaaga tttgattcaa cagaaagttg      240
atgttctgct gatcaatccg gtggatagcc atgcggttgt tacggcgatt aaagaagcga      300
atagcaaaaa tatcccggtt attaccatcg atcgcagcgc gaatggtggt gatgttgttt      360
cccatatcgc cagcgataat gttaagggtg gcgaaatggc cgcggaattt atcgcgaaag      420
ccctgaaagg caaggggaat gttgtggaac tggaagtat cccgggggcg tctgcggcac      480
gtgatcgcgg caagggttt gatgaagcca ttgctaagta tccggatatt aaaatcgttg      540
caaagcaggc ggcggatttt gatcgttcca aggtctgtc agtgatggaa acatcttgc      600 aagcccagcc gaaaattgat gcagtgtttg cgcaaaatga tgaaatggct ctgggcgcta      660
tcaaagccat tgaggccgcg aatcgtcaag gtattattgt tgtgggcttt gatgggaccg      720
aagatgctct gaaagcgatt aaagaaggga aatggctgc gaccattgcg cagcagccgg      780
ccctgatggg ctcactgggt gtggagatgg ctgataaata cctgaaaggt gaaaaaattc      840
cgaactttat tccggcagaa ctgaaactca tcacgaaaga aaatgtgcag ggtgagcgg      900 caagcggggg tgccgcgggt ggcagctctg cggcgcgcct gcaggtcgac aagcttgcgg      960
ccgcattaga agtgctgttt caaggtccag gcatgtgcaa taccaacatg tctgtaccta      1020
ctgatggtgc tgtaaccacc tcacagattc agcttcgga caagagacc ctggttagac      1080 caaagccatt gcttttgaag ttattaaagt ctgttggtgc acaaaaagac acttatacta      1140
tgaaagaggt tctttttat cttggccagt atattatgac taaacgatta tatgatgaga      1200
agcaacaaca tattgtatat tgttcaaatg atcttctagg agatttgttt ggcgtgccaa      1260
gcttctctgt gaaagagcac aggaaaatat ataccatgat ctacaggaac ttggtagtag      1320
tcaatcagca ggaatcatcg gactcaggta catctgtgag tgagaacagg gtcaccttg      1380 aaggtgggag tgatcaaaag gaccttgtac aagagcttca ggaagagaaa ccttcatctt      1440
```

```
cacatttggt ttctagacca tctacctcat ctagaaggag agcaattagt gagacagaag    1500
aaaattcaga tgaattatct ggtgaacgac aaagaaaacg ccacaaatct gatagtattt    1560
ccctttcctt tgatgaaagc ctggctctgt gtgtaataag ggagatatgt tgtgaaagaa    1620
gcagtagcag tgaatctaca gggacgccat cgaatccgga tcttgatgct ggtgtaagtg    1680
aacattcagg tgattggttg gatcaggatt cagtttcaga tcagtttagt gtagaatttg    1740
aagttgaatc tctcgactca gaagattata gccttagtga agaaggacaa gaactctcag    1800
atgaagatga tgaggtatat caagttactg tgtatcaggc aggggagagt gatacagatt    1860
catttgaaga agatcctgaa atttccttag ctgactattg gaaatgcact tcatgcaatg    1920
aaatgaatcc cccccttcca tcacattgca acagatgttg ggcccttcgt gagaattggc    1980
ttcctgaaga taaagggaaa gataaagggg aaatctctga gaaagccaaa ctggaaaact    2040
caacacaagc tgaagagggc tttgatgttc ctgattgtaa aaaaactata gtgaatgatt    2100
ccagagagtc atgtgttgag gaaaatgatg ataaaattac acaagcttca caatcacaag    2160
aaagtgaaga ctattctcag ccatcaactt ctagtagcat tatttatagc agccaagaag    2220
atgtgaaaga gtttgaaagg gaagaaaccc aagacaaaga agagagtgtg gaatctagtt    2280
tgccccttaa tgccattgaa ccttgtgtga tttgtcaagg tcgacctaaa aatggttgca    2340
ttgtccatgg caaaacagga catcttatgg cctgctttac atgtgcaaag aagctaaaga    2400
aaaggaataa gccctgccca gtatgtagac aaccaattca aatgattgtg ctaacttatt    2460
tcccctagct cgagtctggt aaagaaaccg ctgctgcgaa atttgaacgc cagcacatgg    2520
actcgtctac tagcgcagc                                                 2539

<210> SEQ ID NO 17
<211> LENGTH: 35
<212> TYPE: PRT
<213> ORGANISM: artificial sequence
<220> FEATURE:
<223> OTHER INFORMATION: Fusion polypeptide fragment not included

<400> SEQUENCE: 17

Arg Lys Ser Arg Ile Leu Leu Leu Leu Thr Ile Phe Val Thr Ser Ala
1               5                   10                  15

Ala Leu Ile Leu Ser Gly Cys Lys Thr Asn Thr Pro Asn Thr Ala Ser
            20                  25                  30

Thr Ser Thr
        35
```

CLEAVABLE FUSION TAG FOR PROTEIN OVEREXPRESSION AND PURIFICATION

CROSS REFERENCE TO RELATED APPLICATIONS

This application is a continuation of U.S. patent application Ser. No. 15/767,901, filed Apr. 12, 2018, which issued Feb. 12, 2019 as U.S. Pat. No. 10,202,607, and entitled "CLEAVABLE FUSION TAG FOR PROTEIN OVEREXPRESSION AND PURIFICATION." which claims the benefit as a national stage application under 35 U.S.C. 371 of International Application No. PCT/US2016/056832, filed Oct. 12, 2016, which claims priority to U.S. Provisional Application No. 62/240,863, filed Oct. 13, 2015, each of which are incorporated herein by reference.

FIELD

The present disclosure relates generally to compositions and methods for improving recombinant protein production. The recombinant proteins use Ribose Binding Protein for enhancing protein expression.

BACKGROUND

Many naturally occurring proteins and peptides are of great interest in research, medical, and industrial applications, but obtaining them in sufficient quantities from their natural hosts can be problematic because of low purity or natural abundance. Furthermore, engineering the proteins for altered or improved properties is all but impossible in most native hosts (e.g. insulin from pigs or cows). As a result, scientists have turned to recombinant protein expression in model organisms whose genetics can be manipulated to cause overexpression of proteins not natively found in the host.

For technical reasons, microorganisms like *E. coli* and *S. cerevisiae* are the preferred hosts for recombinant protein expression. However, because model microorganisms lack the protein folding machinery and regulatory mechanisms of the organisms from which most proteins of interest originate (e.g. mammals), proteins are often translated poorly or fold improperly from expression constructs (recombinant DNA molecules encoding the protein being produced and other elements necessary for expression), resulting in poor protein expression, solubility and ultimately low yield. There is thus an ongoing and unmet need for improved compositions and methods for improving recombinant protein production.

SUMMARY

The present disclosure encompasses compositions and methods for increasing protein production. In general the compositions and methods include expression vectors, recombinant fusion proteins encoded by them, cells comprising the expression vectors, and isolated/purified recombinant fusion proteins, and fragments thereof. The fusion proteins comprise a polypeptide of interest (also referred to herein as a "target protein") and a segment that comprises a Ribose Binding Protein (RBP), or at least a contiguous portion of an RBP, such that production of the fusion protein is increased. The fusion proteins can be configured to include a segment that is useful for liberating the target protein from the RBP and other non-target protein portions of the fusion protein.

Increases in protein production made possible by the present disclosure can be determined by comparison to any suitable reference, including but not necessarily limited to a value that represents the actual or expected or predicted or calculated expression of the target protein when an RBP segment is not present in the same polypeptide that includes the target protein.

The disclosure is illustrated by non-limiting embodiments that demonstrate RBP-fusion protein production comprising functionally and structurally distinct proteins having different sizes and amino acid profiles. In particular and representative demonstrations, recombinant fusion protein production is illustrated in a prokaryotic system using a modified RBP derived from the RBP produced by *Thermoanaerobacter tengcongensis* (*T. tengcongensis*), but it will be apparent that other RBPs can be substituted. In particular embodiments, the disclosure demonstrates recombinant protein production using RBPs expressed in a single polypeptide with human p53, WD-Repeat Protein 5 (WDR5) from *Drosophila melanogaster*, actin from *Saccharomyces cerevisiae*, human rhinovirus 3C (HRV 3C) protease, and Mouse double minute 2 homolog (MDM2) also known as E3 ubiquitin-protein ligase Mdm2. The MDM2 has the amino acid sequence of the mouse and human proteins, as they are identical. Thus, the disclosure demonstrates broad applicability to express, and increase expression, of a variety of distinct proteins, and it is expected there are no particular limitations to the type of proteins that can be used in one or more embodiments of the invention.

A representative RBP sequence is provided in SEQ ID NO:2. This sequence comprises a Cys102Ser alternation relative to the wild type *T. tengcongensis* sequence. Further, it has been determined that enhanced expression of a target protein as a component of a fusion protein described herein does not require the entire length of the RBP. In this regard, in certain embodiments, the disclosure comprises expression vectors, the proteins encoded by them, and other embodiments, wherein the entire RBP segment is not essential. Additionally, the disclosure differs from other systems that have used RBPs in fusion proteins, such as in domain swapping configurations, because the RBP or a segment thereof is provided sequentially with the target protein. As such, in various implementations, the RBP of this disclosure does not interrupt the target protein. In certain approaches, the disclosure includes expression vectors and the fusion proteins encoded by them, wherein the fusion proteins comprise truncations at the N-terminus of the RBP component of from 1-33 amino acids, inclusive and including all integers and all ranges of integers there between, and/or at the C-terminus of the RBP component of from 1-67 amino acids, inclusive and including all integers and all ranges of integers there between. Accordingly, in one approach the disclosure provides a recombinant expression vector encoding a fusion protein comprising sequentially an RBP segment and an uninterrupted target polypeptide, wherein RBP segment comprises at least 178 contiguous amino acids of SEQ ID NO:2, wherein the segment comprises amino acid number 34 (Gly) of SEQ ID NO:2 and amino acid number 211 (Gln) of SEQ ID NO:2. In certain embodiments the expression vector does not encode a signal peptide that targets the fusion protein to periplasm. In some examples an amino acid linker sequence is encoded between the RBP segment and the target protein. In certain examples at least one amino acid sequence tag for purification of the encoded fusion protein is included. In non-limiting embodiments, the target protein may be the only target protein encoded by the expression vector, or in the fusion protein, and in certain embodiments the RBP segment may be the only RBP segment encoded by the expression vector, or in the fusion protein. In certain approaches the fusion protein comprises an amino acid linker sequence, and the linker sequence may optionally comprises a proteolytic cleavage site, such as to liberate the target protein from the fusion protein by cleavage at the proteolytic cleavage site. In certain examples, the fusion protein does not oligomerize in solution with proteins that have the same amino acid sequence of the fusion protein encoded by the expression vector.

In another aspect the disclosure includes a method of making a recombinant fusion protein. The method comprises providing cells at least some of which comprise an expression vector of this disclosure, and allowing expression of the recombinant fusion protein. The fusion protein can be separated from the cells and if desired purified to any desired degree of purity. The target protein can be separated from the fusion protein by, for example, cleaving the fusion protein using any suitable approach or method, including but not limited to cleavage at a proteolytic cleavage site engineered to separate the RBP and the target protein. In certain approaches a cell culture used to express a fusion protein described herein is prokaryotic cell culture, but eukaryotic cell cultures can also be used.

In another aspect the disclosure comprises a method of making a cell culture that is useful for recombinant protein expression. This method comprises introducing an expression vector into a cell culture. The disclosure accordingly includes such cell cultures, their progeny, and further comprises the media in which any cell culture described herein is cultured in. Also included are cell lysates obtained by lysing any cell or population of cells described herein.

In another aspect the disclosure provides a kit. The kit can comprise, for example, an expression vector described herein, and may optionally comprise a restriction endonuclease that recognizes a restriction endonuclease recognition site positioned between the RBP and the target protein. The kit can also include printed instructions for using the expression vector to express the fusion protein.

The disclosure includes any fusion proteins made using a composition, method, and/or kit described herein, and also includes any target polypeptide cleaved from such a fusion protein.

DETAILED DESCRIPTION

Figure 1:
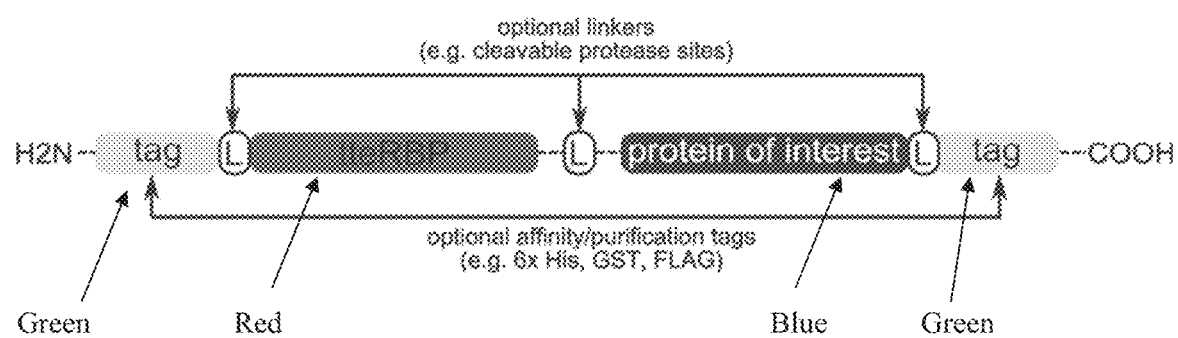
FIG. 1. Schematic representation of resultant fusion protein. The tteRBP tag is shown in red, protein of interest in blue, optional purification tags in green, and optional linker sequences in white. The tteRBP is presented at the N-terminal end of the protein of interest, but it may also be placed at the C-terminal end.
Figure 2:
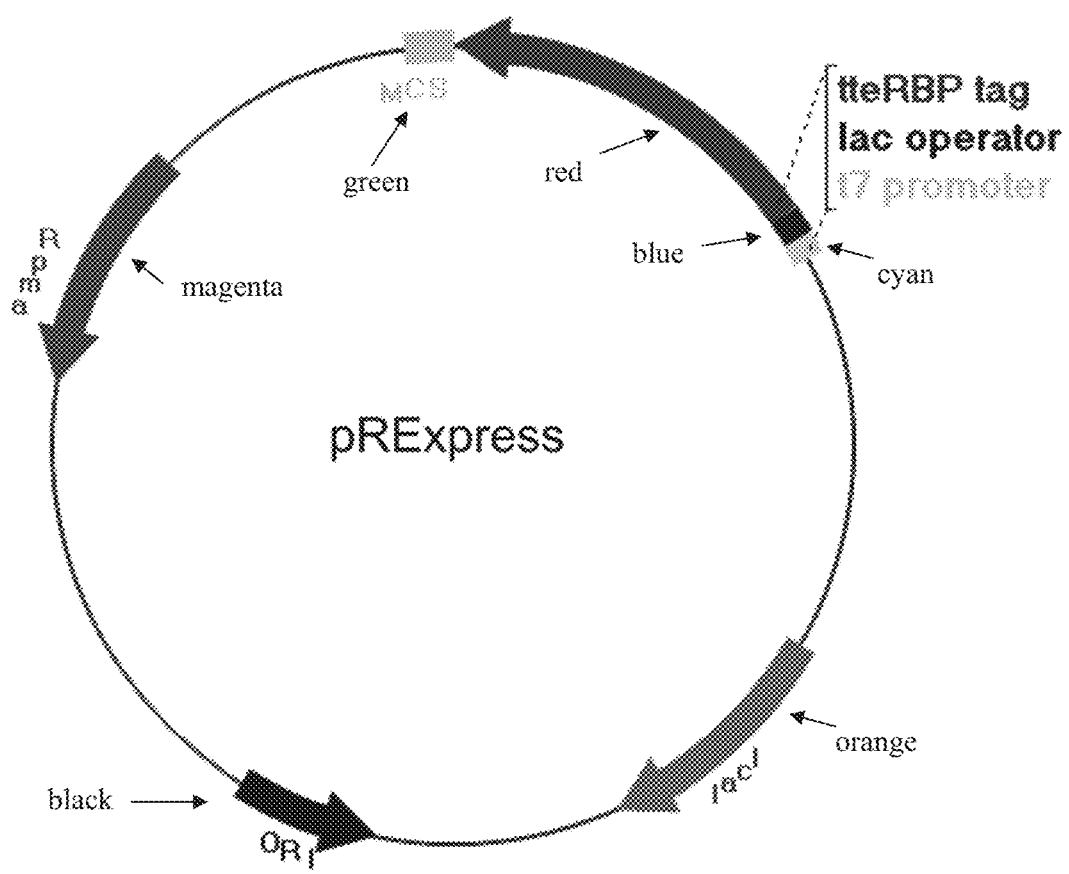
FIG. 2. Schematic of *E. coli* expression plasmid pRExpress. This is a schematic of representative bacterial expression plasmid that comprises the DNA sequence for the tteRBP tag, functional homologue, fragment, or derivative. It includes a representative promoter (e.g. the T7 promoter shown in cyan), and additional expression-control elements required for the particular expression system being used (e.g. the lacI gene (orange) and lac operator (blue)), the tteRBP, functional homologue, fragment, or derivative expression tag (red), a multiple cloning site containing the sequences for restriction endonucleases (green), a selection element such as antibiotic resistance (e.g. the ampR gene shown in magenta), and an origin of replication to allow the cells to synthesize more plasmids as they grow (black). Each of these elements may be tailored to the different expression systems they are being used in (e.g. using the Aox1 or Aox2 promoters instead of T7 promoter for methanol induction in the model organism *Pichia pastoris*).

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

Every DNA sequence disclosed herein includes its complementary DNA sequence, and also includes the RNA equivalents thereof. Every DNA and RNA sequence encoding the polypeptides disclosed herein is encompassed by this disclosure, including but not limited to all fusion proteins, and all of the Ribose Binding Protein (RBP) segment of fusion proteins, including but not limited to those comprising N-terminal and/or C-terminal truncations of the RBP segment.

The present disclosure encompasses compositions and methods for improving production of recombinantly produced protein. In embodiments the disclosure comprises recombinant expression vectors and methods of using them to produce proteins. In general the expression vectors encode at least one fusion protein comprising a segment that includes a polypeptide of interest (also referred to herein as a "target protein") and a segment that comprises a Ribose Binding Protein (RBP) or at least a contiguous portion of an RBP.

In embodiments, the RBP encoded by the expression vector comprises an RBP from a prokaryote, such as an archaea, which may be a thermophilic and/or anaerobic microorganism. In an embodiment, the RBP is from *Thermoanaerobacter tengcongensis* (*T. tengcongensis*), which is referred to herein as "tteRBP." In embodiments, the RBP comprises a functional homologue, fragment, or derivative of tteRBP or a segment thereof which retains the capability to enhance production of a fusion protein into which it is inserted. Enhanced protein production means in one embodiment that more of the fusion protein is produced than a value for a suitable reference. In embodiments, the reference can be a value obtained by production of the protein into which the RBP or segment thereof has not been inserted. In embodiments, the disclosure includes increasing production of a recombinant protein by at least 10% relative to a reference, and can comprise increasing production of a recombinant protein by from 10%-80%, inclusive, relative to a reference, or more than 80% relative to a reference.

In embodiments, the RBP comprises an amino acid sequence that is at least 80% similar to SEQ ID NO:2, or to a contiguous segment of SEQ ID NO:2. In embodiments, the RBP comprises an amino acid sequence that is 90, 91, 92, 93, 94, 95, 96, 97, 98 or 99% identical to SEQ ID NO:2 or a segment of it, for example, a segment that comprises at least 178 amino acids. Thus, in certain embodiments, an RBP segment of this disclosure comprises variations in sequence relative to SEQ ID NO:2. Such variations can comprise conservative or non-conservative amino acid substitutions, insertions, and deletions. In embodiments, the RBP component of the fusion protein comprises a mutation relative to its naturally occurring sequence. In one embodiment the mutation is a Cys102Ser alteration. In certain implementations, the RBP component of a fusion protein lacks a signal peptide, and thus the disclosure also includes entire fusion proteins which lack a signal peptide. The term "lacks a signal peptide" means either the construct may in fact lack the signal peptide sequence, or the signal peptide may simply be modified to lack signal peptide function. In an embodiment, the fusion protein lacks a signal peptide that functions to transport the protein to the periplasm (N-terminal amino acid sequence RKSRILLLLTIFVTSAAL-ILSGCKTNTPNTASTST (SEQ ID NO: 17).

In embodiments the RBP component of the fusion protein is a segment of a full-length RBP (but lacking a signal sequence). We have also determined if 34 or more amino acids are removed from the N-terminus, or 68 or more amino acids are removed from the C-terminus, the protein loses much of its stability and native structure/function as measured by melting temperature, far UV circular dichroism spectrum, 2D NMR spectrum, and ribose binding ability. Thus, it is considered that a truncation of the first 34 or more N-terminal amino acids, or the last 68 or more C-terminal amino acids of SEQ ID NO:2, exceeds the limits of how much the ends of the tteRBP component can be shortened, yet still function to increase expression and solubility. However, an RBP component of the fusion protein that has shorter truncations of amino acids at its N-terminus, its C-terminus, or at both the N- and C-termini, may still have utility as a solubility and expression tag. Therefore, the disclosure includes fusion proteins which comprise truncations at the N-terminus of the RBP component of from 1-33 amino acids, inclusive and including all integers and all ranges of integers there between, and at the C-terminus of the RBP component of from 1-67 amino acids, inclusive and including all integers and all ranges of integers there between.

In embodiments, the RBP component of the fusion protein comprises a contiguous segment of SEQ ID NO:2 that includes amino acid number 34 of SEQ ID NO:2 at its N terminus. In embodiments, the RBP component of the fusion protein comprises a contiguous segment of SEQ ID NO:2 that includes the amino acid at position 211 of SEQ ID NO:2 at its C-terminus. In embodiments, the RBP component of the fusion protein comprises a contiguous segment of SEQ ID NO:2 that comprises or consists of a segment of SEQ ID NO:2 having the amino acid at position 34 and the amino acid at position 211 of SEQ ID NO:2 at its N- and C-terminus, respectively. In embodiments, the RBP component of the fusion protein is from 278 to 211 amino acids in length. In one embodiment, the RBP component is at least 244 amino acids in length. In embodiments, the fusion protein comprises a tteRBP component lacking the signaling peptide and comprising amino acids 1-211, 1-259, or 34-278, of SEQ ID NO:2. SEQ ID NO:2 is: MKEGXTIGLV ISTLNPFFVTKGAWEKLGYKIIVEDSQNDSSKELSNV-EDLIQQKVDVLLINPVDSDAVV TAIKEANSKNIPVITI-DRSANGGDVVSHIASDNVKGGEMIAAEFIAKALKGK GNVVELEGIPGASAARDRGKGFDE AIAKYPDIKIVAK QAADFDRSKGLSVMENILQAQPKIDAVFAQNDEMAL GAIKAIEAANRQGIZVIGDGTEDAL KAIKEGMAATIA QQPALMGSLGVEMADKYLKGEKIPNFIPAELKLITK ENVQ. The bold italicized amino acids indicate those that have been determined in accordance with this invention to be dispensable for use in the enhanced protein production approaches of this disclosure.

In embodiments, the fusion proteins do not comprise ubiquitin. In embodiments the fusion proteins do not comprise any segment of ubiquitin that can enhance production of the fusion protein in which the ubiquitin segment is contained, relative to production of an otherwise same fusion protein but in which the ubiquitin segment is not present. In embodiments the fusion proteins do not comprise a ubiquitin-like protein, Apoptosis Stimulating Protein of p53 2 ("ASPP2"), an isoform of ASPP2, or General Control Protein 4 ("GCN4"). In embodiments the fusion proteins of the present disclosure do not bind to one another in solution, and/or do not oligomerize, and/or do not undergo domain swapping with one another and thus do not bind to other of the same or similar fusion proteins in trans, and/or do not bind to one another in cis. In an embodiment, the fusion proteins do not form a network, such as a branched network, or a gel comprising the fusion proteins. In embodiments, fusion proteins of this disclosure retain their native-like structure, which can be determined, for example, using near-UV circular dichroism spectroscopy (CD), electrophoretic mobility shift assay (EMSA), gel-filtration chromatography, or any other suitable approach for determining protein structure. In embodiments, isolated fusion proteins of this disclosure retain their native-like structure. In embodiments, a fusion protein of this disclosure may comprise only a single RBP, even if the RBP is interrupted by a distinct polypeptide sequence. In embodiments a fusion protein of this disclosure can include only one protein of interest, which may be N-terminal to the RBP segment, C-terminal to the RBP segment, or flanked by RBP segments.

A representative polynucleotide sequence encoding tteRBP is provided in SEQ ID NO: 1. Those skilled in the art will recognize that, due to the redundancy of the genetic code, there are a multitude of polynucleotide sequences that can encode tteRBP, and each of these sequences is included within the scope of this disclosure. This also pertains to the other DNA sequences that encode representative and non-limiting examples of fusion proteins provided by this disclosure as further described in the Examples.

The polypeptide encoded by the expression vector along with the RBP segment may be any polypeptide of interest. A target polypeptide according to the present disclosure may be any polypeptide required or desired in larger amounts and therefore may be difficult to isolate or purify from other sources. Non-limiting examples of target proteins that can produced by the present methods include mammalian gene products, such as enzymes, cytokines, growth factors, hormones, vaccines, antibodies and the like. In embodiments, overexpressed gene products of the present disclosure include gene products such as erythropoietin, insulin, somatotropin, growth hormone releasing factor, platelet derived growth factor, epidermal growth factor, transforming growth factor a, transforming growth factor 13, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin and the like. In embodiments overexpressed gene products are human gene products. The present methods can readily be adapted to enhance secretion of any overexpressed gene product which can be used as a vaccine. Overexpressed gene products which can be used as vaccines include any structural, membrane-associated, membrane-bound or secreted gene product of a mammalian pathogen. Mammalian pathogens include viruses, bacteria, single-celled or multi-celled parasites which can infect or attack a mammal. For example, viral vaccines can include vaccines against viruses such as human immunodeficiency virus (HIV), vaccinia, poliovirus, adenovirus, influenza, hepatitis A, hepatitis B, dengue virus, Japanese B encephalitis, Varicella zoster, cytomegalovirus, hepatitis A, rotavirus, as well as vaccines against viral diseases like measles, yellow fever, mumps, rabies, herpes, influenza, parainfluenza and the like. Bacterial vaccines can include vaccines against bacteria such as *Vibrio cholerae, Salmonella typhi, Bordetella pertussis, Streptococcus pneumoniae, Hemophilus influenza, Clostridium tetani, Corynebacterium diphtheriae, Mycobacterium leprae, R. rickettsii, Shigella, Neisseria gonorrhoeae, Neisseria meningitidis, Coccidioides immitis, Borellia burgdorferi*, and the like. A target polypeptide may also comprise sequences; e.g., diagnostically relevant epitopes, from several different proteins constructed to be expressed as a single recombinant polypeptide.

Variants of the RBP or target protein bearing one or several amino acid substitutions or deletion are also included in this disclosure. The skilled artisan can easily assess whether such variants, e.g., fragments or mutants are appropriate for a method of this disclosure by, for example, using the procedures as described in the Examples.

As described above, in embodiments the present disclosure provides polypeptides comprising at least one polypeptide domain corresponding to the tteRBP used as an expression tool and at least one polypeptide domain corresponding to the target protein. In embodiments, the tteRBP component is referred to as a solubility and expression tag.

A representative and non-limiting configuration of a fusion protein of this disclosure is provided in FIG. 1 wherein the location of an optional linker polypeptide of 10-100 amino acid residues is depicted. As the skilled artisan will appreciate, such a linker polypeptide is designed as most appropriate for the intended application, especially in terms of length, flexibility, charge, and hydrophilicity. E.g., in case of a hydrophobic target protein the linker polypeptide may contain an appropriate number of hydrophilic amino acids. In embodiments the present disclosure also relates to fusion proteins which comprise the target polypeptide and one, or two tteRBP-solubility and expression tag or domains thereof and an appropriate peptidic linker sequences between domains. For such applications where the target protein is desired in free form a linker peptide or linker peptides can be used. Such linkers contain an appropriate proteolytic cleavage site. Peptide sequences appropriate for proteolytic cleavage are well-known to the skilled artisan and comprise amongst others, e.g., Ile-Glu-Gly-Arg, cleaved at the carboxy side of the arginine residue by coagulation factor Xa, or Gly-Leu-Pro-Arg-Gly-Ser, a thrombin cleavage site, etc.

In embodiments the DNA construct of the present disclosure encodes a fusion protein comprising a polypeptide linker in between the polypeptide sequence corresponding to the tteRBP-solubility and expression tag and the polypeptide sequence corresponding to the target protein. Such a DNA sequence coding for a linker, in addition to e.g., providing for a proteolytic cleavage site, may also serve as a polylinker. i.e., it may provide multiple DNA restriction sites to facilitate fusion of the DNA fragments coding for a target protein and a solubility and expression tag domain.

In a further embodiment, the disclosure includes a recombinant DNA molecule, such as an expression vector, encoding a fusion protein, comprising operatively-linked at least one nucleotide sequence coding for a target polypeptide and upstream thereto at least one nucleotide sequence coding for a tteRBP.

Polynucleotide sequences are operatively-linked when they are placed into a functional relationship with another polynucleotide sequence. For instance, a promoter is operatively-linked to a coding sequence if the promoter affects transcription or expression of the coding sequence. Generally, operatively-linked means that the linked sequences are contiguous and, where necessary to join two protein coding regions, both contiguous and in reading frame. However, it is well known that certain genetic elements, such as enhancers, may be operatively-linked even at a distance, i.e., even if not contiguous. Promoters of the present disclosure may be endogenous or heterologous to the host, and may be constitutive or inducible.

DNA constructs prepared for introduction into a host typically comprise a replication system recognized by the host, including the intended DNA fragment encoding the desired target fusion peptide, and will can also include transcription and translational initiation regulatory sequences operatively-linked to the polypeptide encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences.

The appropriate promoter and other necessary vector sequences are selected so as to be functional in the host. Examples of workable combinations of cell lines and expression vectors include but are not limited to those described Sambrook, J., et al., in "Molecular Cloning: A Laboratory Manual" (1989, 4th edition: 2012)-, Eds. J. Sambrook, E. F. Fritsch and T. Maniatis, Cold Spring Harbor Laboratory Press, Cold Spring Harbor, or Ausubel, F., et al., in "Current Protocols in Molecular Biology" (1987 and periodic updates), Eds. F. Ausubel, R Brent and K. R. E., Wiley & Sons Verlag, New York; and Metzger, D., et al., Nature 334 (1988) 31-6. Many useful vectors for expression in bacteria, yeast, mammalian, insect, plant or other cells are known in the art and may be obtained from vendors including, but not limited to. Stratagene, New England Biolabs, Promega Biotech, and others. In addition, the construct may be joined to an amplifiable gene (e.g., DHFE) so that multiple copies of the gene may be obtained.

Expression and cloning vectors can contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g., ampicillin, tetracycline, etc.: (b) complement auxotrophic deficiencies; or (c) supply critical nutrients not available from complex media. The choice of the proper selectable marker will depend on the host cell, and appropriate markers for different hosts are known in the art.

The expression vectors containing the polynucleotides of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses. Large quantities of the polynucleotides and polypeptides may be prepared by expressing the polynucleotides in compatible host cells. The most commonly used prokaryotic hosts are strains of *Escherichia coli*, although other prokaryotes, such as *Bacillus subtilis* may also be used.

Construction of a vector according to the present disclosure employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructions expression vectors, preparing in vitro transcripts, introducing DNA into host cells, and performing analyses for assessing expression and function are known to those skilled in the art.

The DNA construct comprising two solubility and expression tag domains as well as a target polypeptide domain may also contains two linker peptides in between these domains. In order to allow for systematic cloning, the nucleotide sequences coding for these two linker peptide sequences may be different from one another. This difference in nucleotide sequence can result in a difference in the amino-acid sequence of the linker peptides, but the amino acid sequences of the two linker peptides may also be identical. Such identical linker peptide sequences for example are advantageous if the fusion protein comprising two tteRBP-solubility and expression tag domains as well as their target protein domain is to be used in an immunoassay.

In cases where it is desired to release one or all of the solubility and expression tags out of a fusion protein, the linker peptide can be constructed to comprise a proteolytic cleavage site. Thus, a recombinant DNA molecule, such as an expression vector, encoding a fusion protein comprising at least one polynucleotide sequence coding for a target polypeptide, upstream thereto at least one polynucleotide sequence coding for a tteRBP-solubility and expression tag with the signaling peptide removed, and additionally comprising a nucleic acid sequence coding for a peptidic linker comprising a proteolytic cleavage site, represents a non-limiting embodiment of this invention. In certain embodiments, the expression vector comprises codons optimized for expression in the host cell.

The recombinant proteins of the inventions can be recovered by conventional methods. Thus, where the host cell is bacterial, such as *E. coli* it may be lysed physically, chemically or enzymatically and the protein product isolated from the resulting lysate. It is then purified using conventional techniques, including but not necessarily limited to conventional protein isolation techniques such as selective precipitation, adsorption chromatography, and affinity chromatography, including but not limited to a monoclonal antibody affinity column.

In embodiments the fusion proteins comprise a tag for facilitating separation, isolation and/or purification. For example, when the proteins of the present invention are expressed with a histidine tail (HIS tag), they can easily be purified by affinity chromatography using an ion metal affinity chromatography column (IMAC) column.

In one embodiment, the proteins comprise an affinity peptide, such as a Histidine tail, fused at the carboxy-terminus of the proteins of the invention. In embodiments the His tag comprises between 5 to 8 histidine residues, or at least 4 His residues, or 6 His residues. In embodiments the affinity peptide has adjacent histidine residues, such as at least two, three or four. In an embodiment the protein comprises 6 directly neighboring histidine residues. In another embodiment, the proteins comprise a C-LYTA tag at their carboxy-terminus. Lyta is derived from *Streptococcus pneumoniae* which synthesize an N-acetyl-L-alanine amidase, amidase LYTA, (coded by the lytA gene {Gene, 43 (1986) page 265-272} an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at its amino terminus has been described {Biotechnology: 10, (1992) page 795-798}.

When used as part of an expression construct designed for the expression of the coded protein in an appropriate host (e.g. a bacterial expression plasmid in *E. Coli*, pCDFDuet-1 and pET-23 used with BL21(DE3) in Example 1), the disclosure produces a novel fusion protein, from which the protein of interest can be readily purified, in certain embodiments at substantially higher levels than can be achieved using only the sequence for the protein of interest alone.

Fusion polypeptides can be purified to high levels (greater than 80%, or greater than 90% pure, as visualized by SDS-PAGE) by undergoing further purification steps. An additional purification step is a Q-Sepharose step that may be operated either before or after the IMAC column to yield highly purified protein. They present a major single band when analyzed by SDS PAGE under reducing conditions, and western blot analysis show less than 5% host cell protein contamination.

The fusion proteins of the invention may be expressed in unicellular hosts such as prokaryotic and lower eukaryotic organisms, such as yeast and bacteria. In an embodiment the fusion are expressed in *E. coli*.

In one aspect, the present disclosure relates to a method of producing a fusion protein. The method comprises the steps of culturing a host cell transformed with an expression vector as described above, expression of that fusion protein in the respective host cell and separating the protein from the cell culture. The expression system is demonstrated to function with biochemically distinct target proteins, e.g., p53, cellulase 6B and 5A from *Thermobifida fusca* and cellulase from *Pyrococcus horikoshii*, WD-repeat containing protein 5 (WDR5) from *Drosophila melanogaster*, and actin. As can be readily seen from the Examples of this disclosure, specifically relating to these proteins, the efficient expression systems function and result in high levels of fusion protein produced. Similar findings have been made with a variety of other target proteins expressed as fusion proteins.

Further, we demonstrate that the target protein comprised in a fusion protein produced according to the present disclosure can be obtained in a native-like structure. Such native-like structure and function, e.g., for p53 and cellulases, has been confirmed by near-UV circular dichroism spectroscopy (CD), electrophoretic mobility shift assay (EMSA), and gel-filtration chromatography. For p53, near-UV CD spectroscopy reveals a folded protein with mixed alpha helix and beta strand character, EMSA reveals high-affinity site-specific binding to DNA including the p53 consensus recognition sequence, and gel-filtration reveals the correct "tetrameric" oligomeric state, which is well known in the art. Cellulases were confirmed native and functional by cellulose filter paper digestion. Avicel digestion, and soluble carboxymethyl cellulose digestion assays, which are well known cellulase activity assays in the art.

Compositions comprising fusion proteins, or proteins liberated from the tteRBP, are also provided. Such compositions include but are not necessarily limited to compositions that comprise a pharmaceutically acceptable excipient and thus are suitable for human and veterinary prophylactic and/or therapeutic approaches.

In another embodiment, kits for producing fusion proteins according to this disclosure are provided. The kits can provide one or more expression vectors described herein, as well as printed instructions for using the vectors, and/or for recovering the overexpressed protein.

The following specific examples are provided to illustrate the invention, but are not intended to be limiting in any way.

Example 1

This Example demonstrates a fusion protein of the present invention that comprises full length p53 expressed in *E. coli* BL21(DE3).

Expression Plasmids.

The full-length human p53 gene (coding sequence for amino acids 1-393) was fused to the 3' end of either an oligonucleotide coding for an N-terminal 6×His tag followed by the human rhinovirus 3C (HRV 3C) protease recognition site (LEVLFN/GP) and placed under the control of a T7 promoter in the pET23 expression vector (EMD Millipore, Billerica, Mass.), or to the 3' end of an oligonucleotide coding for an N-terminal 6×His tag followed by tteRBP, an linker and a HRV3C protease recognition site and placed under the control of a T7 promoter in the pCDF-Duet1 expression vector (EMD Millipore, Billerica. Mass.). The nucleotide and resultant fusion protein sequences can be seen in Table 1.

Protein Expression and Partial Purification.

BL21(DE3) cells made competent by $CaCl_2$) permeabilization were transformed with the expression plasmids, plated on LB Agar plates containing 50 µg/mL ampicillin (for pET23) or streptomycin (for pCDFDuet-1), and grown at 37° C. for ~18 hrs. Isolated colonies were then picked and grown in batch culture (1 L baffled flasks) at 37° C. in LB containing 50 µg/mL appropriate antibiotic with 200 RPM continuous shaking until $OD_{600}$=0.6. The temperature was then dropped to 20° C. and the cultures induced with 20 mg/L IPTG and grown for 18 hrs. Cells were harvested by centrifugation, resuspended in resuspension/wash buffer (20 mM Tris pH 7.2, 300 mM NaCl, 10 mM Imidazole, and 10 mM β-mercaptoethanol), and lysed by incubation with egg white lysozyme and DNAase I+5 mM $MgCl_2$ on ice for 60 min. Insoluble material was pelleted by centrifugation, and the clarified supernatant loaded on to a $Ni^{2+}$-NTA column pre-equilibrated with resuspension/wash buffer. After washing, the sample was eluted with 20 mM Tris pH 7.2, 300 mM NaCl, 250 mM Imidazole, and 10 mM 3-mercaptoethanol. Protein-containing fractions were then pooled, dialyzed against 20 mM Tris, 150 mM NaCl, 10 mM β-mercaptoethanol, and the tags removed by incubation with GST-tagged HRV 3C protease (0.05-0.1 mg protease/mg p53) for ~18 hrs at 4° C. Samples were subjected to denaturing, reducing SDS-PAGE (samples prepared by boiling in 1× Lamelli Buffer+10% β-mercaptoethanol for 5 min) and visualized by staining with Coumassie Brilliant Blue.

Results

Figure 3:
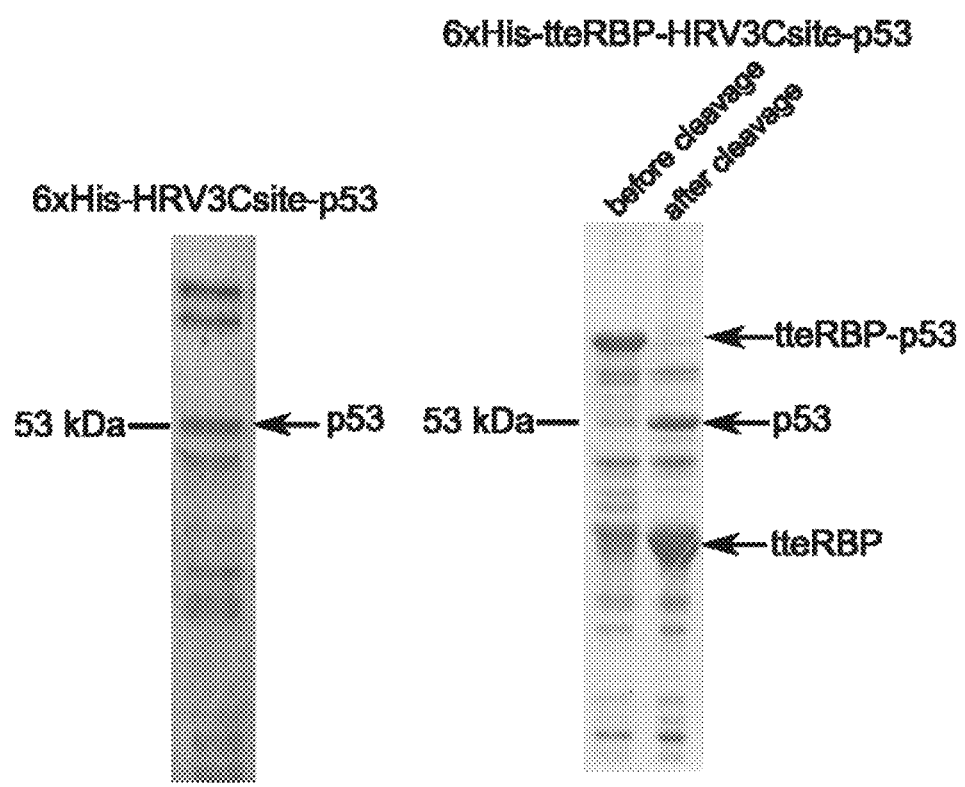
FIG. 3. Full length human p53 gels. Shown is an SDS-PAGE gel of full-length p53 expressed as fusion proteins to either an N-terminal 6×His tag (left) or 6×His-tteRBP tag (right) through a cleavable linker containing the HRV 3C recognition site. Additionally, the gel on the right shows samples taken before and after overnight cleavage with GST-tagged HRC 3C protease. These gels demonstrate a marked increase in soluble expression of the fusion protein.

After $Ni^{2+}$-NTA chromatography, a band corresponding to the correct molecular weight of 6×His-HRV3Csite-p53 or the 6×His-tteRBP-HRV3Csite-p53 fusion protein can be seen. However, the band in the 6×His-HRV3Csite-p53 lane is faint, and is not significantly more intense than many of the impurities (FIG. 3). In the case of the 6×His-tteRBP-HRC3Csite-p53, by far the most intense band is the fusion protein (FIG. 3). After cleavage by HRV 3C protease, a band corresponding the correct molecular weight of liberated p53 and the tteRBP tag appear, and the band corresponding to the fusion protein disappears (FIG. 3). A gel for the cleaved product for 6×His-HRV3Csite-p53 is not shown because the tag is too small (~1.4 kDa) to resolve "cleaved" from "uncleaved" protein by SDS-PAGE. After further purification the 6×His-tteRBP-HRV3Csite-p53 system gave a final yield of 3 mg/L culture of >90% pure p53 by SDS-PAGE and gel filtration (not shown). 6×His-HRV3Csite-p53 gave an estimated yield of <0.1 mg/L culture ~50% pure by SDS-PAGE and gel filtration (not shown). Together, these data demonstrate a >30-fold increase in yield and an 80% increase in purity for recombinant human p53 by employing the modified tteRBP tag in *E. coli*.

Example 2

This example demonstrates tteRBP as an expression tag for WD-Repeat Protein 5 (WDR5) from *Drosophila melanogaster* in *E. coli*.

Expression Plasmids

The coding sequence for WDR5 from *Drosophila melanogaster* was fused to the 3' end of either an oligonucleotide coding for an N-terminal 6×His tag and placed under the control of a T7 promoter in the pHis-parallel1 expression vector (NCBI GenBank AF097413.1), or to the 3' end of an oligonucleotide coding for an N-terminal 6×His tag followed by tteRBP, an linker and a HRV3C protease recognition site and placed under the control of a T7 promoter in the pCDF-Duet1 expression vector (EMD Millipore, Billerica, Mass.). The nucleotide and resultant fusion protein sequences can be seen in Table 1.

Protein Expression and Purification

BL21(DE3) cells made competent by $CaCl_2$) permeabilization were transformed with the expression plasmids, plated on LB Agar plates containing 50 µg/mL streptomycin for pCDF-Duet1 or ampicillin for pHis-parallel1, and grown at 37° C. for ~18 hrs. Isolated colonies were then picked and grown in batch culture (5 mL tubes) at 37° C. in LB containing 50 µg/mL streptomycin 50 µg/mL streptomycin for pCDF-Duet1 or ampicillin for pHis-parallel1 with 200 RPM continuous shaking until $OD_{600}$=0.6. Cultures were induced with 20 mg/L IPTG and grown at for ~18 hrs. Samples taken before induction and after 18 hrs induction were lysed by boiling in cracking buffer (1× lamelli buffer+4

M Urea+10% β-mercaptoethanol) for 5 min, and subjected to SDS-PAGE. Whole cell lysates were then visualized by staining with Coumassie Brilliant Blue.

Results

Figure 4:
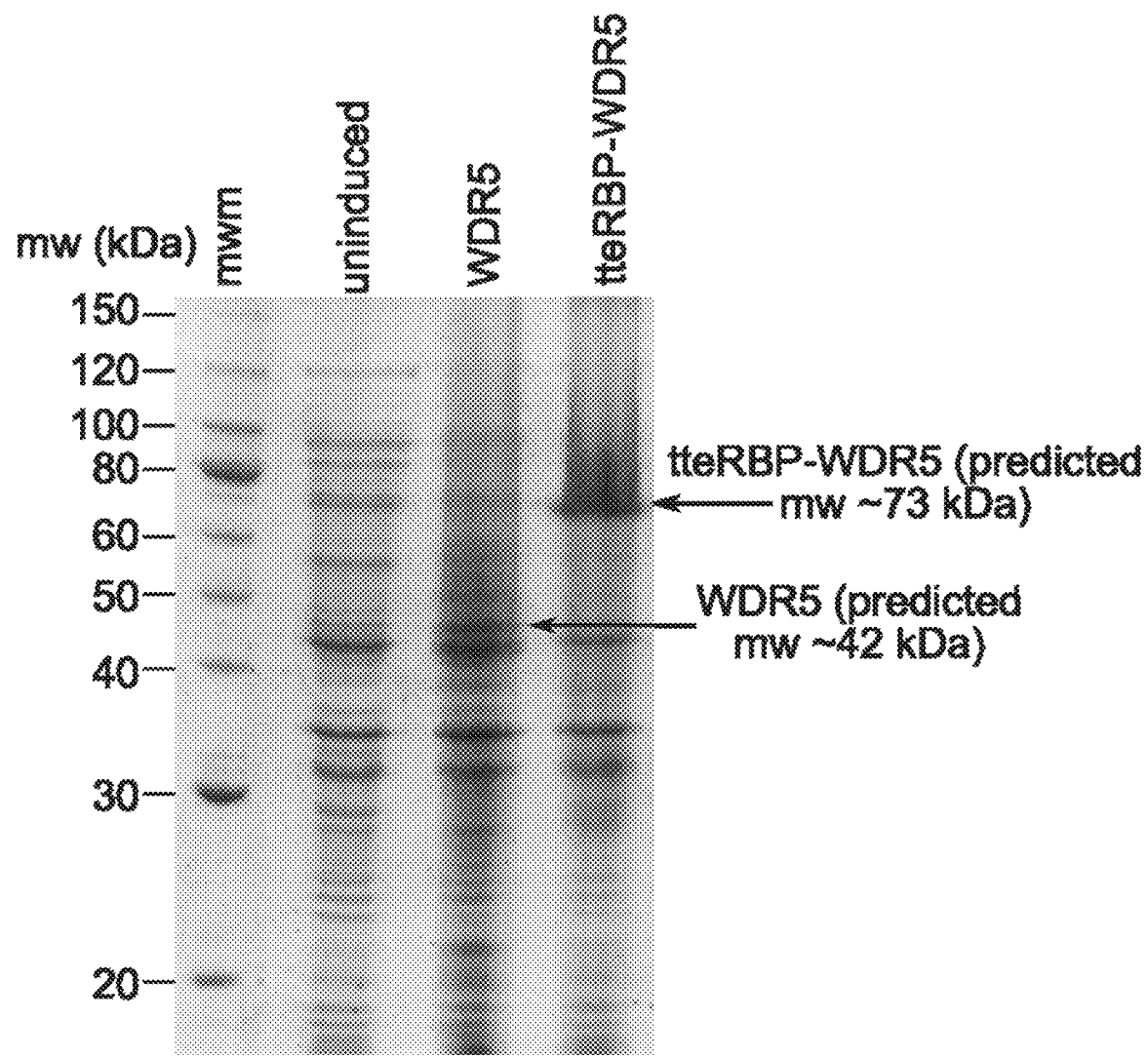
FIG. 4. Shown is an SDS-PAGE gel of whole cell lysates of uninduced BL21 (DE3) with WDR5 expressed alone, or as a tteRBP fusion protein (both proteins contained N-terminal 6×His tags). Molecular weight standard is the CLEARLY protein ladder (Unstained) (Clontech Laboratories Inc., Mountain View, Calif.). This figure clearly demonstrates that the fusion protein expresses at substantially higher levels than the unfused WDR5.

Bands corresponding to the predicted molecular weight of both the untagged and tteRBP tagged proteins can be seen in their respective lanes that are not present in the uninduced sample (FIG. 4). However, the band corresponding to the fusion protein is much more intense, indicating that it expressed at a much higher level than the untagged protein. In combination with other data in this work, this indicates that tteRBP can enhance the expression of many diverse proteins.

Example 3

This Example demonstrates use of tteRBP as an expression tag in *E. coli* BL21(DE3) for the expression of Actin.

Expression Plasmids

The full-length human actin gene was fused to the 3' end of an oligonucleotide coding for an N-terminal 6×His tag followed by tteRBP, an linker and a HRV3C protease recognition site and placed under the control of a T7 promoter in the pCDF-Duet 1 expression vector (EMD Millipore, Billerica, Mass.). The nucleotide and resultant fusion protein sequences can be seen in Table 1.

Protein Expression

BL21(DE3) cells made competent by $CaCl_2$ permeabilization were transformed with the expression plasmids, plated on LB Agar plates containing 50 μg/mL streptomycin, and grown at 37° C. for ~18 hrs. Isolated colonies were then picked and grown in batch culture (50 mL unbaffled flasks) at 37° C. in LB containing 50 μg/mL streptomycin with 225 RPM continuous shaking until $OD_{600}$=0.6. Cultures were then cooled to 20° C. and induced with 20 mg/L IPTG and grown at for 18 hrs. Cells were harvested by centrifugation, resuspended in resuspension/wash buffer (20 mM Tris pH 7.2, 300 mM NaCl, 10 mM Imidazole, and 10 mM β-mercaptoethanol), and lysed by incubation with egg white lysozyme and DNAase I+5 mM $MgCl_2$ on ice for 60 min. The fusion protein expressed as inclusion bodies, which were pelleted by centrifugation and washed 3 times in buffer and 1 M NaCl. The pellet was then dissolved in 20 mM Tris pH 7.2, 300 mM NaCl, 10 mM Imidazole, 10 mM β-mercaptoethanol+6 M guanidine-hydrochloride and loaded onto an $Ni^{2+}$-NTA column pre-equilibrated with the same buffer. After washing, the sample was eluted with 20 mM Tris pH 7.2, 300 mM NaCl, 250 mM Imidazole, and 10 mM 3-mercaptoethanol. Protein-containing fractions were then pooled, and refolded by 20-fold rapid dilution into 20 mM Tris, 150 mM NaCl, 10 mM β-mercaptoethanol. Samples were subjected to denaturing, reducing SDS-PAGE (samples prepared by boiling in 1× Lamelli Buffer+10% β-mercaptoethanol for 5 min) and visualized by staining with Coumassie Brilliant Blue.

Results

The resultant protein was soluble and resulted in a single homogenous band by SDS-PAGE. This is a substantial improvement over previous attempts at IPTG-inducible recombinant expression of human actin in *E. coli*, which has previously been demonstrated to yield little to no soluble protein at these temperatures [Production of human beta actin and a mutant using bacterial expression system with a cold shock vector, Tamura M et al, Protein Expression and Purification (2010)].

Example 4

This example demonstrates a fusion protein of the present invention that comprises and RBP fusion with HRV3C protease.

Expression Plasmid

The sequence for HRV3C protease was fused to the 3' end of an oligonucleotide coding for an N-terminal 6×His tag followed by tteRBP and placed under the control of a T7 promoter in the pCDF-Duet1 expression vector (EMD Millipore, Billerica, Mass.).

Protein Expression and Purification

BL21(DE3) cells made competent by $CaCl_2$) permeabilization were transformed with the expression plasmids, plated on LB Agar plates containing 50 μg/mL streptomycin and grown at 37° C. for ~18 hrs. Isolated colonies were then picked and grown in batch culture (1 L baffled flasks) at 37° C. in LB containing 50 μg/mL streptomycin with 200 RPM continuous shaking until $OD_{600}$=0.6. The temperature was then dropped to 18° C. and the cultures induced with 20 mg/L IPTG and grown for ~18 hrs. Cells were harvested by centrifugation, resuspended in resuspension/wash buffer (20 mM Tris pH 8.0, 300 mM NaCl. 10 mM Imidazole, and 10 mM-mercaptoethanol), and lysed by incubation with egg white lysozyme and DNAase I+5 mM $MgCl_2$ on ice for 60 min. Insoluble material was pelleted by centrifugation, and the clarified supernatant loaded on to a $Ni^{2+}$-NTA column pre-equilibrated with resuspension/wash buffer. After washing, the sample was eluted with 20 mM Tris pH 8.0, 300 mM NaCl, 250 mM Imidazole, and 10 mM β-mercaptoethanol. Protein-containing fractions were then pooled, dialyzed against 20 mM Tris, 10 mM β-mercaptoethanol. Samples were then further purified by Q-sepharose chromatography in the same buffer with a 0-1M NaCl gradient. Samples were subjected to denaturing, reducing SDS-PAGE (samples prepared by boiling in 1× Lamelli Buffer+10% β-mercaptoethanol for 5 min) and visualized by staining with Coumassie Brilliant Blue. Precision protease (GST-fused HRV3C protease) was obtained from GE Healthcare Life Sciences for comparison.

Results

Figure 5:
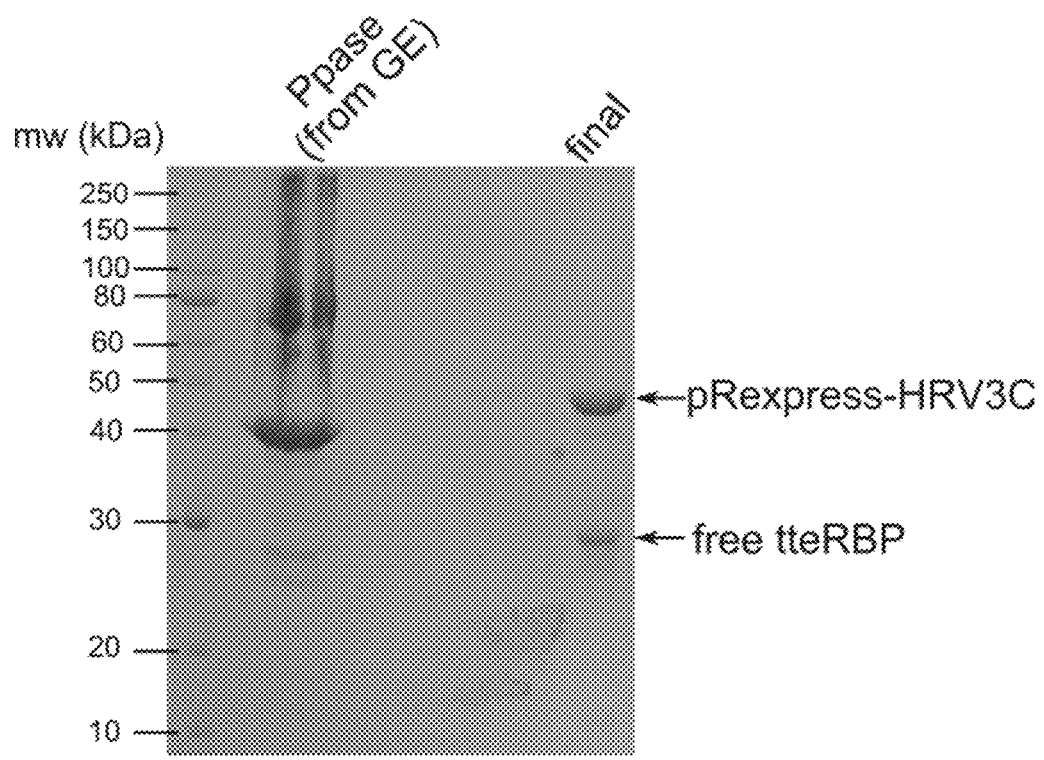
FIG. 5. Shown is an SDS-PAGE gel of HRV3C protease purified using our system purified using the GST-tag obtained from a commercial source. Molecular weight standard is the CLEARLY protein ladder (unstained) (Clontech Laboratories Inc., Mountain View, Calif.). This figure demonstrates that the fusion protein of tteRBP and HRV3C protease can be expressed and purified from *E. coli*.

We were able to purify a protein was purified with a molecular weight consistent with the fusion protein, with the only major impurity being a band with a molecular weight consistent with the free-RBP tag (FIG. 5). This protein was purified in yields of >10 mg/L. This demonstrates the use of an embodiment of this disclosure to express and purify proteases in high yield. The results are shown in FIG. 5, which depicts an SDS-PAGE gel of HRV3C protease purified using our pRexpress system. The fusion protein included a GST-tag obtained from a commercial source. The molecular weight standard is the CLEARLY protein ladder (unstained) (Clontech Laboratories Inc., Mountain View, Calif.). Thus, the example demonstrates a fusion protein of tteRBP and HRV3C protease can be expressed and purified from *E. coli* using a non-limiting embodiment of this disclosure.

Example 5

This example demonstrates an RBP fusion protein that comprises full length MDM2, a ubiquitin E3 ligase.

Expression Plasmid.

The full-length human MDM2 gene was fused to the 3' end of an oligonucleotide coding for an N-terminal 6×His tag followed by tteRBP, an linker and a HRV3C protease recognition site and placed under the control of a T7 promoter in the pCDF-Duet1 expression vector (EMD Millipore, Billerica, Mass.).

Protein Expression and Purification

BL21(DE3) cells made competent by CaCl$_2$) permeabilization were transformed with the expression plasmid, plated on LB Agar plates containing 50 µg/mL streptomycin, and grown at 37° C. for ~18 hrs. Isolated colonies were then picked and grown in batch culture (1 L baffled flasks) at 37° C. in LB containing 50 g/mL streptomycin with 200 RPM continuous shaking until OD$_{600}$=0.6. The temperature was then dropped to 18° C. and the cultures induced with 20 mg/L IPTG and grown for ~18 hrs. Cells were harvested by centrifugation, resuspended in resuspension/wash buffer (20 mM Tris pH 8.0, 300 mM NaCl. 10 mM Imidazole, and 10 mM-mercaptoethanol), and lysed by incubation with egg white lysozyme and DNAase I+5 mM MgCl$_2$ on ice for 60 min. Insoluble material was pelleted by centrifugation, and the clarified supernatant loaded on to a Ni$^{2+}$-NTA column pre-equilibrated with resuspension/wash buffer. After washing, the sample was subjected to on-column tag cleavage with GST-tagged HRV 3C protease (0.05-0.1 mg protease/mg p53) for ~18 hrs at 4° C. The protein was then collected, and samples were subjected to denaturing, reducing SDS-PAGE (samples prepared by boiling in 1× Lamelli Buffer+ 10% 3-mercaptoethanol for 5 min) and visualized by staining with Coumassie Brilliant Blue.

Results

We were able to purify a protein that migrated at a molecular weight consistent with MDM2. We were able to confirmed its identity by western blot, and also found that this protein bound to full-length p53. Thus, this example demonstrates yet another embodiment of this disclosure in the form of an RBP/MDM2 fusion protein.

Table 1. Representative nucleotide and protein sequences used in this disclosure. In amino acid sequences below, the tteRBP amino acid sequences are italicized, amino acid sequences of proteins of interest are underlined, amino acid sequences of additional purification tags (e.g. 6×His) show in bold, and amino acid sequences of linkers are shown in plain text (without italics, without underlining, and not it bold). Additionally, protease recognition sequences within linkers are shown with a double underline.

```
DNA coding sequence of modified tteRBP for use as an expression and
solubility tag
                                                             (SEQ ID NO: 1)
    1    ATGAAAGAGG GCAAAACGAT TGGCCTGGTG ATCTCTACCC TGAACAATCC GTTCTTTGTG

61    ACCCTGAAAA ATGGTGCGGA AGAAAAAGCG AAAGAACTGG GTTACAAAAT TATCGTTGAA

121    GATTCGCAAA ATGATTCCTC TAAAGAGCTG TCTAATGTCG AAGATTTGAT TCAACAGAAA

181    GTTGATGTTC TGCTGATCAA TCCGGTGGAT AGCGATGCGG TTGTTACGGC GATTAAAGAA

241    GCGAATAGCA AAAATATCCC GGTTATTACC ATCGATCGCA GCGCGAATGG TGGTGATGTT

301    GTTTCCCATA TCGCCAGCGA TAATGTTAAG GGTGGCGAAA TGGCCGCGGA ATTTATCGCG

361    AAAGCCCTGA AAGGCAAGGG GAATGTTGTG GAACTGGAAG GGATCCCGGG GGCGTCTGCG

421    GCACGTGATC GCGGCAAAGG GTTTGATGAA GCCATTGCTA AGTATCCGGA TATTAAAATC

481    GTTGCAAAGC AGGCGGCGGA TTTTGATCGT TCCAAAGGTC TGTCAGTGAT GGAAAACATC

541    TTGCAAGCCC AGCCGAAAAT TGATGCAGTG TTTGCGCAAA ATGATGAAAT GGCTCTGGGC

601    GCTATCAAAG CCATTGAGGC CGCGAATCGT CAAGGTATTA TTGTTGTGGG CTTTGATGGG

661    ACCGAAGATG CTCTGAAAGC GATTAAAGAA GGGAAAATGG CTGCGACCAT TGCGCAGCAG

721    CCGGCCCTGA TGGGCTCACT GGGTGTGGAG ATGGCTGATA AATACCTGAA AGGTGAAAAA

781    ATTCCGAACT TTATTCCGGC AGAACTGAAA CTCATCACGA AAGAAAATGT GCAG

Amino acid sequence of modified tteRBP for use as an expression and
solubility tag
                                                             (SEQ ID NO: 2)
MKEGKTIGLVISTLNNPFFVTLKNGAEEKAKELGYKIIVEDSQNDSSKELSNVEDLIQQK

VDVLLINPVDSDAVVTAIKEANSKNIPVITIDRSANGGDVVSHIASDNVKGGEMAAEFIA

KALKGKGNVVELEGIPGASAARDRGKGFDEAIAKYPDIKIVAKQAADFDRSKGLSVMENI

LQAQPKIDAVFAQNDEMALGAIKAIEAANRQGIIVVGFDGTEDALKAIKEGKMAATIAQQ

PALMGSLGVEMADKYLKGEKIPNFIPAELKLITKENVQ

DNA coding sequence of tteRBP-p53 fusion protein used in
Example 1 (SEQ ID NO: 3):
    1    ATGGGCAGCA GCCATCACCA TCATCACCAC AGCCAGGATC CGAATTCGAG CTCGATGAAA

61    GAGGGCAAAA CGATTGGCCT GGTGATCTGT ACCCTGAACA ATGCGTTCTT TGTGACCCTG

121    AAAAATGGTG CGGAAGAAAA AGCGAAAGAA CTGGGTTACA AAATTATCGT TGAAGATTCG

181    CAAAATGATT CCTCTAAAGA GCTGTCTAAT GTCGAAGATT TGATTCAACA GAAAGTTGAT
```

-continued

```
 241   GTTCTGCTGA TCAATCCGGT GGATAGCGAT GCGGTTGTTA CGGCGATTAA AGAAGCGAAT
 301   AGCAAAAATA TCCCGGTTAT TACCATCGAT CGCAGCGCGA ATGGTGGTGA TGTTGTTTCC
 361   CATATCGCCA GCGATAATGT TAAGGGTGGC GAAATGGCCG CGGAATTTAT CGCGAAAGCC
 421   CTGAAAGGCA AGGGGAATGT TGTGGAACTG GAAGGTATCC CGGGGGCGTC TGCGGCACGT
 481   GATCGCGGCA AAGGGTTTGA TGAAGCCATT GCTAAGTATC CGGATATTAA AATCGTTGCA
 541   AAGCAGGCGG CGGATTTTGA TCGTTCCAAA GGTCTGTCAG TGATGGAAAA CATCTTGCAA
 601   GCCCAGCCGA AAATTGATGC AGTGTTTGCG CAAAATGATG AAATGGCTCT GGGCGCTATC
 661   AAAGCCATTG AGGCCGCGAA TCGTCAAGGT ATTATTGTTG TGGGCTTTGA TGGGACCGAA
 721   GATGCTCTGA AAGCGATTAA AGAAGGGAAA ATGGCTGCGA CCATTGCGCA GCAGCCGGCC
 781   CTGATGGGCT CACTGGGTGT GGAGATGGCT GATAAATACC TGAAAGGTGA AAAAATTCCG
 841   AACTTTATTC CGGCAGAACT GAAACTCATC ACGAAAGAAA ATGTGCAGGG TGGAGCGGCA
 901   AGCGGGGGTG CCGCGGGTGG CAGCTCTGCG GCGCGCCTGC AGGTCGACAA GCTTGCGGCC
 961   GCATTAGAAG TGCTGTTTCA AGGTCCAGGC ATGGAGGAGC CGCAGTCAGA TCCTAGCGTC
1021   GAGCCCCCTC TGAGTCAGGA ACATTTTGA GACCTATGGA AACTACTTCC TGAAAACAAC
1081   GTTCTGTCCC CCTTGCCGTC CCAAGCAATG GATGATTTGA TGCTGTCCCC GGACGATATT
1141   GAACAATGGT TCACTGAAGA CCCAGGTCCA GATGAAGCTC CCAGAATGCC AGAGGCTGCT
1201   CCCCCCGTGG CCCCTGCACC AGCAGCTCCT ACACCGGCGG CCCCTGCACC AGCCCCCTCC
1261   TGGCCCCTGT CATCTTCTGT CCCTTCCCAG AAAACCTACC AGGGCAGCTA CGGTTTCCGT
1321   CTGGGCTTCT TGCATTCTGG GACAGCCAAG TCTGTGACTT GCACGTACTC CCCTGCCCTC
1381   AACAAGATGT TTTGCCAACT GGCCAAGACC TGCCCTGTGC AGCTGTGGGT TGATTCCACA
1441   CCCCCGCCCG GCACCCGCGT CCGCGCCATG GCCATCTACA AGCAGTCACA GGACATGACG
1501   GAGGTTGTGA GGCGCTGCCC CCACCATGAG CGCTGCTCAG ATAGGGATGG TCTGGCCCCT
1561   CCTCAGCATC TTATCCGAGT GGAAGGAAAT TTGCGTGTGG AGTATTTGGA TGACAGAAAC
1621   ACTTTTGGAC ATAGTGTGGT GGTGCCCTAT GAGCCGCCTG AGGTTGGCTC TGACTGTACC
1581   ACCATCCACT ACAACTACAT GTGTAACAGT TCCTGCATGG GCGGCATGAA CCGGAGGCCC
1741   ATCCTCACCA TCATCACACT GGAAGACTCC AGTGGTAATC TACTGGGACG AACAGCTTT
1801   GAGGTGCGTG TTTGTGCCTG TCCTGGGAGA GACCGGCGCA CAGAGGAAGA GAATCTCCGC
1861   AAGAAAGGGG AGCCTCACCA CGAGCTGCGC CCAGGGAGCA CTAAGCGAGC ACTGCCCAAC
1921   AACACCAGCT CCTGTCCCCA GCCAAAGAAG AAACCACTGG ATGGAGAATA TTTCACCCTT
1981   CAGATCCGTG GGCGTGAGCG CTTCGAGATG TTCCGAGAGC TGAATGAGGC CTTGGAACTC
2041   AAGGATGCCC AGGCTGGGAA GGAGCCAGGG GGGAGCAGGG CTCACTCCAG CCACCTGAAG
2101   TCCAAAAAGG GTCAGTCTAC CTCCCGCCAT AAAAAACTCA TGTTCAAGAC AGAAGGGCCT
2161   GACTCAGACT GAC
```

Amino acid sequence of the tteRBP-p53 fusion protein used in Example 1 (SEQ ID NO: 4):
MGSSHHHHHHSQDPNSSSMKEGKTIGLVISTLNNPFFVTLKNGAEEKAKELGYKIIVEDS

QNDSSKELSNVEDLIQQKVDVLLINPVDSDAVVTAIKEANSKNIPVITIDRSANGGDVVS

HIASDNVKGGEMAAEFIAKALKGKGNVVELEGIPGASAARDRGKGFDEAIAKYPDIKIVA

KQAADFDRSKGLSVMENILQAQPKIDAVFAQNDEMALGAIKAIEAANRQGIIVVGFDGTE

DALKAIKEGKMAATIAQQPALMGSLGVEMADKYLKGEKIPNFIPAELKLITKENVQGGAA

SGGAAGGSSAARLQVDKLAAA<u>LEVLFQGPG</u>MEEPQSDPSVEPPLSQETFSDLWKLLPENN

-continued

VLSPLPSQAMDDLMLSPDDIEQWFTEDPGPDEAPRMPEAAPPVAPAPAAPTPAAPAPAPS

WPLSSSVPSQKTYQGSYGFRLGFLHSGTAKSVTCTYSPALNKMFCQLAKTCPVQLWVDST

PPPGTRVRAMAIYKQSQHMTEVVRRCPHHERCSDSDGLAPPQHLIRVEGNLRVEYLDDRN

TFRHSVVVPYEPPEVGSDCTTIHYNYMCNSSCMGGMNRRPILTIITLEDSSGNLLGRNSF

EVRVCACPGRDRRTEEENLRKKGEPHHELPPGSTKRALPNNTSSSPQPKKKPLDGEYFTL

QIRGRERFEMFRELNEALELKDAQAGKEPGGSRAHSSHLKSKKGQSTSRHKKLMFKTEGP

DSD

DNA coding sequence of 6xHis-p53 protein without tteRBP tag
used in Example 1 (SEQ ID NO: 5):

```
  1   ATGCACCATC ACCACCATCA CCTGGAAGTT CTGTTCCAGG GGCCCATGGA GGAGCCGCAG

61   TCAGATCCTA GCGTCGAGCC CCCTCTGAGT CAGGAAACAT TTTCAGACCT ATGGAAACTA

121   CTTCCTGAAA ACAACGTTCT GTCCCCCTTG CCGTCCCAAG CAATGGATGA TTTGATGCTG

181   TCCCCGGACG ATATTGAACA ATGGTTCACT GAAGACCCAG GTCCAGATGA AGCTCCCAGA

241   ATGCCAGAGG CTGCTCCCCC CGTGGCCCCT GCACCAGCAG CTCCTACACC GGCGGCCCCT

301   GCACCAGCCC CCTCCTGGCC CCTGTCATCT TCTGTCCCTT CCCAGAAAAC CTACCAGGGC

361   AGCTACGGTT TCCGTCTGGG CTTCTTGCAT CTGGGACAG CCAAGTCTGT GACTTGCACG

421   TACTCCCCTG CCCTCAACAA GATGTTTTGC CAACTGGCCA AGACCTGCCC TGTGCAGCTG

481   TGGGTTGATT CCACACCCCC GCCCGGCACC CGCGTCCGCG CCATGGCCAT CTACAAGCAG

541   TCACAGCACA TGACGGAGGT TGTGAGGCGC TGCCCCCACC ATGAGCGCTG CTCAGATAGC

601   GATGGTCTGG CCCCTCCTCA GCATCTTATC CGAGTGGAAG GAAATTTGCG TGTGGAGTAT

661   TTGGATGACA GAAACACTTT TCGACATAGT GTGGTGGTGC CCTATGAGCC GCCTGAGGTT

721   GGCTCTGACT GTACCACCAT CCACTACAAC TACATGTGTA ACAGTTCCTG CATGGGCGGC

781   ATGAACCGGA GGCCCATCCT CACCATCATC ACACTGGAAG ACTCCAGTGG TAATCTACTG

841   GGACGAACA GCTTTGAGGT GCGTGTTTGT GCCTGTCCTG GGAGAGACCG GCGCACAGAG

901   GAAGAGAATC TCCGCAAGAA AGGGGAGCCT CACCACGAGC TGCCCCCAGG GAGCACTAAG

961   CGAGCACTGC CAACAACAC CAGCTCCTCT CCCAAGCCAA GAAGAAACC ACTGGATGGA

1021  GAATATTTCA CCCTTCAGAT CCGTGGGCGT GAGCGCTTCG AGATGTTCCG AGAGCTGAAT

1081  GAGGCCTTGG AACTCAAGGA TGCCCAGGCT GGGAAGGAGC CAGGGGGGAG CAGGGCTCAC

1141  TCCAGCCACC TGAAGTCCAA AAAGGGTCAG TCTACCTCCC GCCATAAAA ACTCATGTTC

1201  AAGACAGAAG GGCCTGACTC AGACTGA
```

Amino acid sequence of the 6xHis-p53 fusion protein without tteRBP
tag used in Example 1:

(SEQ ID NO: 6)

MHHHHHHLEVLFQGPMEEPQSDPSVEPPLSQETFSDLWKLLPENNVLSPLPSQAMDDLML

SPDDIEQWFTEDPGPDEAPRMPEAAPPVAPAPAAPTPAAPAPAPSWPLSSSVPSQKTYQG

SYGFRLGFLHSGTAKSVTCTYSPALNKMFCQLAKTCPVQLWVDSTPPPGTRVRAMAIYKQ

SQHMTEVVRRCPHHERCSDSDGLAPPQHLIRVEGNLRVEYLDDRNTFRHSVVVPYEPPEV

GSDCTTIHYNYMCNSSCMGGMNRRPILTIITLEDSSGNLLGRNSFEVRVCACPGRDRRTE

EENLRKKGEPHHELPPGSTKRALPNNTSSSPQPKKKPLDGEYFTLQIRGRERFEMFRELN

EALELKDAQAGKEPGGSRAHSSHLKSKKGQSTSRHKKLMFKTEGPDSD

DNA coding sequence of 6xHis-WDR5 fusion protein used in Example 2

(SEQ ID NO: 7)

```
  1   ATGGTCGTACT ACCATCACCA TCACCATCAC GATTACGATA TCCCAACGAC CGAAAACCTG

61   TATTTTCAGG GCGCCATGGA TATGGTGCCC ATCGGAGCCG TGCACGGCGG CCATCCCGGC
```

-continued

```
 121    GTAGTGCATC CGCCACAGCA ACCACTGCCC ACGGCGCCCA GCGGCCCAAA CTCGCTGCAG
 181    CCGAACTCGG TGGGCCAGCC GGGGGCCACC ACCTCCTCGA ACAGCAGCGC CTCCAACAAG
 241    AGCTCGCTAT CCGTCAAGCC CAACTACACG CTCAAGTTCA CGCTGGCCGG GCACACCAAG
 301    GCGGTGTCGG CGGTCAAGTT CAGTCCGAAT GGCGAGTGGC TGGCCAGCTC CTCCGCTGAT
 361    AAACTAATCA AATCTGGGG AGCATACGAT GGCAAGTTCG AGAAGACCAT TTCGGGCCAC
 421    AAGCTGGGCA TCAGCGATGT GGCCTGGAGC TCAGACTCGC GACTCCTCGT GAGCGGCAGT
 481    GATGACAAGA CGCTCAAGGT CTGGGAGCTG AGCACCGGGA AGAGCTTGAA AACTCTGAAG
 541    GGCCACAGCA ACTATGTGTT CTGCTGCAAC TTTAATCCGC AGTCCAATCT GATCGTCTCC
 601    GGCAGCTTCG ACGAGAGCGT TCGCATATGG GATGTGCGCA CCGGCAAGTG TCTGAAGACT
 661    CTACCCGCCC ATTCCGATCC CGTTTCGGCG GTACATTTCA ATCGCGACGG ATCGCTGATC
 721    GTGAGCAGCA GCTACGACGG CCTCTGTCGC ATATGGGACA CGGCCAGTGG ACAGTGCTTG
 781    AAAACCCTGA TCGACGACGA CAATCCGCCC GTCAGCTTTG TAAAGTTCTC GCCCAATGGC
 841    AAGTACATTT TGGCCGCCAC GCTGGATAAT ACGCTCAAGT TGTGGGACTA CTCGAAGGGC
 901    AAGTGCCTGA AGACGTATAC GGGTCACAAG AATGAGAAGT ACTGCATATT CGCCAACTTC
 961    TCGGTGACGG GAGGAAAGTG GATCGTGAGT GGCAGCGAGG ACAACATGGT CTACATTTGG
1021    AATCTGCAGA GCAAGGAGGT GGTGCAAAAG CTGCAGGGAC ACACCGATAC CGTTCTGTGC
1081    ACCGCCTGCC ATCCCACGGA GAACATCATT GCTTCCGCGG CGCTCGAGAA CGACAAGACC
1141    ATCAAGCTGT GGAAGTCGGA TACATAG
```

Amino acid sequence of 6xHis-WDR5 fusion protein used in Example 2
(SEQ ID NO: 8)

MSYYHHHHHHDYDIPTTENLYFQGAMD<u>MVPIGAVHGGHPGVVHPPQQPLPTAPSGPNSLQ</u>
<u>PNSVGQPGATTSSNSSASNKSSLSVKPNYTLKFTLAGHTKAVSAVKFSPNGEWLASSSAD</u>
<u>KLIKIWGAYDGKFEKTISGHKLGISDVAWSSDSRLLVSGSDDKTLKVWELSTGKSLKTLK</u>
<u>GHSNYVFCCNFNPQSNLIVSGSFDESVRIWDVRTGKCLKTLPAHSDPVSAVHFNRDGSLI</u>
<u>VSSSYDGLCRIWDTASGQCLKTLIDDDNPPVSFVKFSPNGKYILAATLDNTLKLWDYSKG</u>
<u>KCLKTYTGHKNEKYCIFANFSVTGGKWIVSGSEDNMVYIWNLQSKEVVQKLQGHTDTVLC</u>
<u>TACHPTENIIASAALENDKTIKLWKSDT</u>

DNA coding sequence of 6xHis-tteRBP-WDR5 fusion protein used in Example 3
(SEQ ID NO: 9)

```
  1    ATGGGCAGCA GCCATCACCA TCATCACCAC AGCCAGGATC CGAATTCGAG CTCGATGAAA
 61    GAGGGCAAAA CGATTGGCCT GGTGATCTCT ACCCTGAACA ATCCGTTCTT TGTGACCCTG
121    AAAAATGGTG CGGAAGAAAA AGCGAAAGAA CTGGGTTACA AAATTATCGT TGAAGATTCG
181    CAAAATGATT CCTCTAAAGA GCTGTCTAAT GTCGAAGATT TGATTCAACA GAAAGTTGAT
241    GTTCTGCTGA TCAATCCGGT GGATAGCGAT GCGGTTGTTA CGGCGATTAA GAAAGCGAAT
301    AGCAAAAATA TCCCGGTTAT TACCATCGAT CGCAGCGCGA ATGGTGGTGA TGTTGTTTCC
361    CATATCGCCA GCGATAATGT TAAGGGTGGC GAAATGGCCG CGGAATTTAT CGCGAAAGCC
421    CTGAAAGGCA AGGGGAATGT TGTGGAACTG GAAGGTATCC CGGGGGCGTC TGCGGCACGT
481    GATCGCGGCA AAGGGTTTGA TGAAGCCATT GCTAAGTATC CGGATATTAA ATCGTTGCA
541    AAGCAGGCGG CGGATTTTGA TCGTTCCAAA GGTCTGTCAG TGATGGAAAA CATCTTGCAA
601    GCCCAGCCGA AAATTGATGC AGTGTTTGCG CAAAATGATG AAATGGCTCT GGGCGCTATC
661    AAAGCCATTG AGGCCGCGAA TCGTCAAGGT ATTATTGTTG TGGGCTTTGA TGGGACCGAA
721    GATGCTCTGA AGCGATTAA AGAAGGGAAA ATGGCTGCGA CCATTGCGCA GCAGCCGGCC
781    CTGATGGGCT CACTGGGTGT GGAGATGGCT GATAAATACC TGAAAGGTGA AAAAATTCCG
```

```
 841    AACTTTATTC CGGCAGAACT GAAACTCATC ACGAAAGAAA ATGTGCAGGG TGGAGCGGCA

901    AGCGGGGGTG CCGCGGGTGG CAGCTCTGCG GCCGCATTAG AAGTGCTGTT TCAAGGTCCA

961    GGCATGGTGC CCATCGGAGC CGTGCACGGC GGCCATCCCG GCGTAGTGCA TCCGCCACAG

1021    CAACCACTGC CCACGGCGCC CAGCGGCCCA AACTCGCTGC AGCCGAACTC GGTGGGCCAG

1081    CCGGGGGCCA CCACCTCCTC GAACAGCAGC GCCTCCAACA GAGCTCGCT ATCCGTCAAG

1141    CCCAACTACA CGCTCAAGTT CACGCTGGCC GGGCACACCA AGGCGGTGTC GGCGGTCAAG

1201    TTCAGTCCGA ATGGCGAGTG GCTGGCCAGC TCCTCCGCTG ATAAACTAAT CAAAATCTGG

1261    GGAGCATACG ATGGCAAGTT CGAGAAGACC ATTTCGGGCC ACAAGCTGGG CATGAGCGAT

1321    GTGGCCTGGA GCTCAGACTC GCGACTCCTC GTGAGCGGCA GTGATGAGAA GACGCTCAAG

1381    GTCTGGGAGC TGAGCACCGG AAAGAGCTTG AAAACTCTGA AGGGCCACAG CAACTATGTG

1441    TTCTGCTGCA ACTTTAATCC GCAGTCCAAT CTGATCGTCT CCGGCAGCTT CGACGAGAGC

1501    GTTCGCATAT GGGATGTGCG CACCGGCAAG TGTCTGAAGA CTCTACCCGC CCATTCCGAT

1561    CCCGTTTCGG CGGTACATTT CAATCGCGAC GGATCGCTGA TCGTGAGCAG CAGCTACGAC

1621    GGCCTCTGTC GCATATGGGA CACGGCCAGT GGACAGTGCT GAAAACCCT GATCGACGAC

1681    GACAATCCGC CCGTCAGCTT TGTAAAGTTC TCGCCCAATG GCAAGTACAT TTTGGCCGCC

1741    ACGCTGGATA ATACGCTCAA GTTGTGGGAC TACTCGAAGG GCAAGTGCCT GAAGACGTAT

1801    ACGGGTCACA GAATGAGAA GTACTGCATA TTCGCCAACT TCTCGGTGAC GGGAGGAAAG

1861    TGGATCGTGA GTGGCAGCGA GGACAACATG GTCTACATTT GGAATCTGCA GAGCAAGGAG

1921    GTGGTGCAAA AGCTGCAGGG ACACACCGAT ACCGTTCTGT GCACCGCCTG CCATCCCACG

1981    GAGAACATCA TTGCTTCCGC GGCGCTCGAG AACCACAAGA CCATCAAGCT GTGGAAGTCG

2041    GATACATAG
```

Amino acid sequence sequence of 6xHis-tteRBP-WDR5 fusion protein used in Example 2

(SEQ ID NO: 10)

MGSSHHHHHHSQDPNSSSMKEGKTIGLVISTLNNPFFVTLKNGAEEKAKELGYKIIVEDS

QNDSSKELSNVEDLIQQKVDVLLINPVDSDAVVTAIKEANSKNIPVITIDRSANGGDVVS

HIASDNVKGGEMAAEFIAKALKGKGNVVELEGIPGASAARDRGKGFDEAIAKYPDIKIVA

KQAADFDRSKGLSVMENILQAQPKIDAVFAQNDEMALGAIKAIEAANRQGIIVVGFDGTE

DALKAIKEGKMAATIAQQPALMGSLGVEMADKYLKGEKIPNFIPAELKLITKENVQGGAA

SGGAAGGSSAAA<u>LEVLFQGPG</u>MVPIGAVHGGHPGVVHPPQQPLPTAPSGPNSLQPNSVGQ

PGATTSSNSSASNKSSLSVKPNYTLKFTLAGHTKAVSAVKFSPNGEWLASSSADKLIKIW

GAYDGKFEKTISGHKLGISDVAWSSDSRLLVSGSDDKTLKVWELSTGKSLKTLKGHSNYV

FCCNFNPQSNLIVSGSFDESVRIWDVRTGKCLKTLPAHSDPVSAVHFNRDGSLIVSSSYD

GLCRIWDTASGQCLKTLIDDDNPPVSFVKFSPNGKYILAATLDNTLKLWDYSKGKCLKTY

AALENDKTIKLWKSDT

Coding nucleotide sequence for tteRBP-actin fusion used in Example 3 (SEQ ID NO: 11):

```
  1    ATGGGCAGCA GCCATCACCA TCATCACCAC AGCCAGGATC CGAATTCGAG CTCGATGAAA

61    GAGGGCAAAA CGATTGGCCT GGTGATCTCT ACCCTGAACA ATCCGTTCTT TGTGACCCTG

121    AAAAATGGTG CGGAAGAAAA AGCGAAAGAA CTGGGTTACA AAATTATCGT TGAAGATTCG

181    CAAAATGATT CCTCTAAAGA GCTGTCTAAT GTCGAAGATT TGATTCAACA GAAAGTTGAT

241    GTTCTGCTGA TCAATCCGGT GGATAGCGAT GCGGTTGTTA CGGCGATTAA AGAAGCGAAT

301    AGCAAAAATA TCCCGGTTAT TACCATCGAT CGCAGCGCGA ATGGTGGTGA TGTTGTTTCC
```

-continued

```
 361   CATATCGCCA GCGATAATGT TAAGGGTGGC GAAATGGCCG CGGAATTTAT CGCGAAAGCC
 421   CTGAAAGGCA AGGGGAATGT TGTGGAACTG GAAGGTATCC CGGGGGCGTC TGCGGCACGT
 481   GATCGCGGCA AAGGGTTTGA TGAAGCCATT GCTAAGTATC CGGATATTAA AATCGTTGCA
 541   AAGCAGGCGG CGGATTTTGA TCGTTCCAAA GGTCTGTCAG TGATGGAAAA CATCTTGCAA
 601   GCCCAGCCGA AAATTGATGC AGTGTTTGCG CAAAATGATG AAATGGCTCT GGGCGCTATC
 661   AAAGCCATTG AGGCCGCGAA TCGTCAAGGT ATTATTGTTG GGGCTTTGA TGGGACCGAA
 721   GATGCTCTGA AAGCGATTAA AGAAGGGAAA ATGGCTGCGA CCATTGCGCA GCAGCCGGCC
 781   CTGATGGGCT CACTGGGTGT GGAGATGGCT GATATATACC TGAAAGGTGA AAAAATTCCG
 841   AACTTTATTC CGGCAGAACT GAAACTCATC ACGAAAGAAA ATGTGCAGGG TGGAGCGGCA
 901   AGCGGGGGTG CCGCGGGTGG CAGCTCTGCG GCCGCATTAG AAGTGCTGTT TCAAGGTCCA
 961   GGCATGGATT CTGAGGTTGC TGCTTTGGTT ATTGATAACG GTTCTGGTAT GTGTAAAGCC
1021   GGTTTTGCCG GTGACGACGC TCCTCGTGCT GTCTTCCCAT CTATCGTCGG TAGACCAAGA
1081   CACCAAGGTA TCATGGTCGG TATGGGTCAA AAAGACTCCT ACGTTGGTGA TGAAGCTCAA
1141   TCCAAGAGAG GTATCTTGAC TTTACGTTAC CCAATTGAAC ACGGTATTGT CACCAACTGG
1201   GACGATATGG AAAAGATCTG GCATCATACC TTCTACAACG AATTGAGAGT TGCCCCAGAA
1261   GAACACCCTG TTCTTTTGAC TGAAGCTCCA ATGAACCCTA ATCAAACAG AGAAAAGATG
1321   ACTCAAATTA TGTTTGAAAC TTTCAACGTT CCAGCCTTCT ACGTTTCCAT CCAAGCCGTT
1381   TTGTCCTTGT ACTCTTCCGG TAGAACTACT GGTATTGTTT TGGATTCCGG TGATGGTGTT
1441   ACTCACGTCG TTCCAATTTA CGCTGGTTTC TCTCTACCTC ACGCCATTTT GAGAATCGAT
1501   TTGGCCGGTA GAGATTTGAC TGACTACTTG ATGAAGATCT TGAGTGAACG TGGTTACTCT
1561   TTCTCCACCA CTGCTGAAAG AGAAATTGTC CGTGACATCA AGGAAAAACT ATGTTACGTC
1621   GCCTTGGACT TCGAACAAGA AATGCAAACC GCTGCTCAAT CTTCTTCAAT TGAAAAATCC
1681   TACGAACTTC CAGATGGTCA AGTCATCACT ATTGGTAACG AAAGATTCAG AGCCCCAGAA
1741   GCTTTGTTCC ATCCTTCTGT TTTGGGTTTG GAATCTGCCG GTATTGACCA AACTACTTAC
1801   AACTCCATCA TGAAGTGTGA TGTCGATGTC CGTAAGGAAT TATACGGTAA CATCGTTATG
1861   TCCGGTGGTA CCACCATGTT CCCAGGTATT GCCGAAAGAA TGCAAAAGGA AATCACCGCT
1921   TTGGCTCCAT CTTCCATGAA GGTCAAGATC ATTGCTCCTC AGAAAGAAA GTACTCCGTC
1981   TGGATTGGTG GTTCTATCTT GGCTTCTTTG ACTACCTTCC AACAAATGTG GATCTCAAAA
2041   CAAGAATACG ACGAAAGTGG TCCATCTATC GTTCACCACA GTGTTTCTA A
```

Amino acid sequence for tteRBP-actin fusion used in Example 3
(SEQ ID NO: 12)

MGSSHHHHHHSQDPNSSSMKEGKTIGLVISTLNNPFFVTLKNGAEEKAKELGYKIIVEDS

QNDSSKELSNVEDLIQQKVDVLLINPVDSDAVVTAIKEANSKNIPVITIDRSANGGDVVS

HIASDNVKGGEMAAEFIAKALKGKGNVVELEGIPGASAARDRGKGFDEAIAKYPDIKIVA

KQAADFDRSKGLSVMENILQAQPKIDAVFAQNDEMALGAIKAIEAANRQGIIVVGFDGTE

DALKAIKEGKMAATIAQQPALMGSLGVEMADKYLKGEKIPNFIPAELKLITKENVQGGAA

SGGAAGGSSAAA<u>LEVLFQGPG</u>MDSEVAALVIDNGSGMCKAGFAGDDAPRAVFPSIVGRPR

HQGIMVGMGQKDSYVGDEAQSKRGILTLRYPIEHGIVTNWDDMEKIWHHTFYNELRVAPE

EHPVLLTEAPMNPKSNREKMTQIMFETFNVPAFYVSIQAVLSLYSSGRTTGIVLDSGDGV

THVVPIYAGFSLPHAILRIDLAGRDLTDYLMKILSERGYSFSTTAEREIVRDIKEKLCYV

ALDFEQEMQTAAQSSSIEKSYELPDGQVITIGNERFRAPEALFHPSVLGLESAGIDQTTY

-continued

NSIMKCDVDVRKELYGNIVMSGGTTMFPGIAERMQKEITALAPSSMKVKIIAPPERKYSV
WIGGSILASLTTFQQMWISKQEYDESGPSIVHHKCF

RBP/HRV3C Fusion Protein Amino Acid Sequence (SEQ ID NO: 13):
MGSSHHHHHHSQDPNSSSMKEGKTIGLVISTLNNPFFVTLKNGAEEKAKELGYKIIVEDS

QNDSSKELSNVEDLIQQKVDVLLINPVDSDAVVTAIKEANSKNIPVITIDRSANGGDVVS

HIASDNVKGGEMAAEFIAKALKGKGNVVELEGIPGASAARDRGKGFDEAIAKYPDIKIVA

KQAADFDRSKGLSVMENILQAQPKIDAVFAQNDEMALGAIKAIEAANRQGIIVVGFDGTE

DALKAIKEGKMAATIAQQPALMGSLGVEMADKYLKGEKIPNFIPAELKLITKENVQGGAA

SGGAAGGSSAAAGGPNTEFALSLLRKNIMTITTSKGEFTGLGIHDRVCVIPTHAQPGDDV

LVNGQKIRVKDKYKLVDPENINLELTVLTLDRNEKFRDIRGFISEDLEGVDATLVVHSNN

FTNTILEVGPVTMAGLINLSSTPTNRMIRYDYATKTGQCGGVLCATGKIFGIHVGGNGRQ

GFSAQLKKQYFVEKQ

RBP/HRV3C Fusion Protein DNA coding sequence
(SEQ ID NO: 14)

```
   1    ATGGGCAG CAGCCATCAC CATCATCACC ACAGCCAGGA TCCGAATTCG
  51    AGCTCGATGA AAGAGGGCAA AACGATTGGC CTGGTGATCT CTACCCTGAA
 101    CAATCCGTTC TTTGTGACCC TGAAAAATGG TGCGGAAGAA AAAGCGAAAG
 151    AACTGGGTTA CAAAATTATC GTTGAAGATT CGCATAATGA TTCCTCTAAA
 201    GAGCTGTCTA ATGTCGAAGA TTTGATTCAA CAGAAAGTTG ATGTTCTGCT
 251    GATCAATCCG GTGGATAGCG ATGCGGTTGT TACGGCGATT AAAGAAGCGA
 301    ATAGCAAAAA TATCCCGGTT ATTACCATCG ATCGCAGCGC GAATGGTGGT
 351    GATGTTGTTT CCCATATCGC CAGCGATAAT GTTAAGGGTG GCGAAATGGC
 401    CGCGGAATTT ATCGCGAAAG CCCTGAAAGG CAAGGGGAAT GTTGTGGAAC
 451    TGGAAGGTAT CCCGGGGGCG TCTGCGGCAC GTGATCGCGG CAAAGGGTTT
 501    GATGAAGCCA TTGCTAAGTA TCCGGATATT AAAATCGTTG CAAAGCAGGC
 551    GGCGGATTTT GATCGTTCCA AAGGTCTGTC AGTGATGGAA ACATCTTGC
 601    AAGCCCAGCC GAAAATTGAT GCAGTGTTTG CGCATAATGA TGAAATGGCT
 651    CTGGGCGCTA TCAAAGCCAT TGAGGCCGCG AATCGTCAAG GTATTATTGT
 701    TGTGGGCTTT GATGGGACCG AAGATGCTCT GAAAGCGATT AAAGAAGGGA
 751    AAATGGCTGC GACCATTGCG CAGCAGCCGG CCCTGATGGG CTCACTGGGT
 801    GTGGAGATGG CTGATAAATA CCTGAAAGGT GAAAAAATTC CGAACTTTAT
 851    TCCGGCAGAA CTGAAACTCA TCACGAAAGA AAATGTGCAG GGTGGAGCGG
 901    CAAGCGGGGG TGCCGCGGGT GGCAGCTCTG CGGCCGCAGG CGGACCAAAC
 951    ACAGAATTTG CACTATCCCT GTTAAGGAAA AACATAATGA CTATAACAAC
1001    CTCAAAGGGA GAGTTCACAG GGTTAGGCAT ACATGATCGT GTCTGTGTGA
1051    TACCCACACA CGCACAGCCT GGTGATGATG TACTAGTGAA TGGTCAGAAA
1101    ATTAGAGTTA AGGATAAGTA CAAATTAGTA GATCCAGAGA ACATTAATCT
1151    AGAGCTTACA GTGTTGACTT TAGATAGAAA TGAAAAATTC AGAGATATCA
1201    GGGGATTTAT ATCAGAAGAT CTAGAAGGTG TGGATGCCAC TTTGGTAGTA
1251    CATTCAAATA ACTTTACCAA CACTATCTTA GAAGTTGGCC CTGTAACAAT
1301    GGCAGGACTT ATTAATTTGA GTAGCACCCC CACTAACAGA ATGATTCGTT
1351    ATGATTATGC AACAAAAACT GGGCAGTGTG GAGGTGTGCT GTGTGCTACT
```

```
                               -continued
1401    GGTAAGATCT TTGGTATTCA TGTTGGCGGT AATGGAAGAC AAGGATTTTC

1451    AGCTCAACTT AAAAAACAAT ATTTTGTAGA GAAACAATAA
```

RBP/MDM2 fusion protein amino acid sequence (SEQ ID NO: 15):
MGSSHHHHHHSQDPNSSS*MKEGKTIGLVISTLNNPFFVTLKNGAEEKAKE*

*LGYKIIVEDSQNDSSKELSNVEDLIQQKVDVLLINPVDSDAVVTAIKEAN*

*SKNIPVITIDRSANGGDVVSHIASDNVKGGEMAAEFIAKALKGKGNVVEL*

*EGIPGASAARDRGKGFDEAIAKYPDIKIVAKQAADFDRSKGLSVMENILQ*

*AQPKIDAVFAQNDEMALGAIKAIEAANRQGIIVVGFDGTEDALKAIKEGK*

*MAATIAQQPALMGSLGVEMADKYLKGEKIPNFIPAELKLITKENVQGGAA*

*SGGAAGGSSAARLQVDKLAAA*<u>LEVLFQGPGMCNTNMSVPTDGAVTTSQIP</u>

<u>ASEQETLVRPKPLLLKLLKSVGAQKDTYTMKEVLFYLGQYIMTKRLYDEK</u>

<u>QQHIVYCSNDLLGDLFGVPSFSVKEHRKIYTMIYRNLVVVNQQESSDSGT</u>

<u>SVSENRCHLEGGSDQKDLVQELQEEKPSSSKLVSRPSTSSRRRAISETEE</u>

<u>NSDELSGERQRKRHKSDSISLSFDESLALCVIREICCERSSSSESTGTPS</u>

<u>NPDLDAGVSEHSGDWLDQDSVSDQFSVEFEVESLDSEDYSLSEEGQELSD</u>

<u>EDDEVYQVTVYQAGESDTDSFEEDPEISLADYWKCTSCNEMNPPLPSHCN</u>

<u>RCWALRENWLPEDKGKDKGEISEKAKLENSTQAEEGFDVPDCKKTIVNDS</u>

<u>RESCVEENDDKITQASQSQESEDYSQPSTSSSIIYSSQEDVKEFEREETQ</u>

<u>DKEESVESSLPLNAIEPCVICQGRPKNGCIVHGKTGHLMACFTCAKKLKK</u>

<u>RNKPCPVCRQPIQMIVLTYFP</u>

RBP/MDM2 fusion protein Fusion protein coding nucleotide
sequence (SEQ ID NO: 16):
```
  1     CCATGGGCAG CAGCCATCAC CATCATCACC ACAGCCAGGA TCCGAATTCG

51     AGCTCGATGA AAGAGGGCAA AACGATTGGC CTGGTGATCT CTACCCTGAA

101     CAATCCGTTC TTTGTGACCC TGAAAAATGG TGCGGAAGAA AAAGCGAAAG

151     AACTGGGTTA CAAAATTATG GTTGAAGATT CGCAAAATGA TTCCTCTAAA

201     GAGCTGTCTA ATGTCGAAGA TTTGATTCAA CAGAAAGTTG ATGTTCTGCT

251     GATCAATCCG GTGGATAGCG ATGCGGTTGT TACGGCGATT AAAGAAGCGA

301     ATAGCAAAAA TATCCCGGTT ATTACCATCG ATCGCAGCGC GAATGGTGGT

351     GATGTTGTTT CCCATATCGC CAGCGATAAT GTTAAGGGTG GCGAAATGGC

401     CGCGGAATTT ATCGCGAAAG CCCTGAAAGG CAAGGGGAAT GTTGTGGAAC

451     TGGAAGGTAT CCCGGGGGCG TCTGCGGCAC GTGATCGCGG CAAAGGGTTT

501     GATGAAGCCA TTGCAAAGTA TCCGGATATT AAAATCGTTG CAAAGCAGGC

551     GGCGGATTTT GATCGTTCCA AAGGTCTGTC AGTGATGGAA AACATCTTGC

601     AAGCCCAGCC GAAAATTGAT GCAGTGTTTG CGCAAAATGA TGAAATGGCT

651     CTGGGCGCTA TCAAAGCCAT TGAGGCCGCG AATCGTCAAG GTATTATTGT

701     TGTGGGCTTT GATGGGACCG AAGATGGTCT GAAAGCGATT AAAGAAGGGA

751     AAATGGCTGC GACCATTGCG CAGCAGCCGG CCCTGATGGG CTCACTGGGT

801     GTGGAGATGG CTGATAAATA CCTGAAAGGT GAAAAAATTC CGAACTTTAT

851     TCCGGCAGAA CTGAAACTCA TCACGAAAGA AAATGTGCAG GGTGGAGCGG

901     CAAGCGGGGG TGCCGCGGGT GGCAGCTCTG CGGCGCGCCT GCAGGTCGAC

951     AAGCTTGCGG CCGCATTAGA AGTGCTGTTT CAAGGTCCAG GCATGTGCAA
```

-continued

```
1001  TACCAACATG TCTGTACCTA CTGATGGTGC TGTAACCACC TCACAGATTC
1051  CAGCTTCGGA ACAAGAGACC TGGTTAGAC CAAAGCCATT GCTTTTGAAG
1101  TTATTAAAGT CTGTTGGTGC ACAAAAAGAC ACTTATACTA TGAAAGAGGT
1151  TCTTTTTTAT CTTGGCCAGT ATATTATGAC TAAACGATTA TATGATGAGA
1201  AGCAACAACA TATTGTATAT TGTTCAAATG ATCTTCTAGG AGATTTGTTT
1251  GGCGTGCCAA GCTTCTCTGT GAAAGAGCAC AGGAAAATAT ATACCATGAT
1301  CTACAGGAAC TTGGTAGTAG TCAATCAGCA GGAATCATCG GACTCAGGTA
1351  CATCTGTGAG TGAGAACAGG TGTCACCTTG AAGGTGGGAG TGATCAAAAG
1401  GACCTTGTAC AAGAGCTTCA GGAAGAGAAA CCTTCATCTT CACATTTGGT
1451  TTCTAGACCA TCTACCTCAT CTAGAAGGAG AGCAATTAGT GAGACAGAAG
1501  AAAATTCAGA TGAATTATCT GGTGAACGAC AAAGAAAACG CCACAAATCT
1551  GATAGTATTT CCCTTTCCTT TGATGAAAGC CTGGCTCTGT GTGTAATAAG
1601  GGAGATATGT TGTGAAAGAA GCAGTAGCAG TGAATCTACA GGGACGCCAT
1651  CGAATCCGGA TCTTGATGCT GGTGTAAGTG AACATTCAGG TGATTGGTTG
1701  GATCAGGATT CAGTTTCAGA TCAGTTTAGT GTAGAATTTG AAGTTGAATC
1751  TCTCGACTCA GAAGATTATA GCCTTAGTGA AGAAGGACAA GAACTCTCAG
1801  ATGAAGATGA TGAGGTATAT CAAGTTACTG TGTATCAGGC AGGGGAGAGT
1851  GATACAGATT CATTTGAAGA AGATCCTGAA ATTTCCTTAG CTGACTATTG
1901  GAAATGCACT TCATGCAATG AAATGAATCC CCCCCTTCCA TCACATTGCA
1951  ACAGATGTTG GGCCCTTCGT GAGAATTGGC TTCCTGAAGA TAAAGGGAAA
2001  GATAAAGGGG AAATCTCTGA GAAAGCCAAA CTGGAAAACT CAACACAAGC
2051  TGAAGAGGGC TTTGATGTTC CTGATTGTAA AAAAACTATA GTGAATGATT
2101  CCAGAGAGTC ATGTGTTGAG CAAAATGATG ATAAAATTAC ACAAGCTTCA
2151  CAATCACAAG AAAGTGAAGA CTATTCTCAG CCATCAACTT CTAGTAGCAT
2201  TATTTATAGC AGCCAAGAAG ATGTGAAAGA GTTTGAAAGG GAAGAAACCC
2251  AAGAGAAAGA AGAGAGTGTG GAATCTAGTT TGCCCCTTAA TGCCATTGAA
2301  CCTTGTGTGA TTTGTCAAGG TCGACCTAAA AATGGTTGCA TTGTCCATGG
2351  CAAAACAGGA CATCTTATGG CCTGCTTTAC ATGTGCAAAG AAGCTAAAGA
2401  AAAGGAATAA GCCCTGCCCA GTATGTAGAC AACCAATTCA AATGATTGTG
2451  CTAACTTATT TCCCCTAGCT CGAGTCTGGT AAAGAAACCG CTGCTGCGAA
2501  ATTTGAACGC CAGCACATGG ACTCGTCTAC TAGCGCAGC
```

While the invention has been described through specific embodiments, routine modifications will be apparent to those skilled in the art and such modifications are intended to be within the scope of the present invention.

---

The invention claimed is:

1. A fusion protein comprising:
   a target protein segment; and
   a Ribose Binding Protein (RBP) segment comprising a contiguous portion of a RBP amino acid sequence, wherein the contiguous portion is at least 80% similar to amino acids 34-211 of SEQ ID NO:2, the fusion protein does not include a signal peptide, at least 80% identical to SEQ ID NO: 17, that targets the fusion protein to the periplasm, and wherein the target protein is operatively linked to an N-terminal or C-terminal end of RBP for protein overexpression.

2. The fusion protein of claim 1, wherein the target protein is operatively linked to the N-terminal end of the RBP segment.

3. The fusion protein of claim 1, further comprising a linker peptide segment positioned between the target protein segment and the RBP segment and configured to liberate the target protein segment from the RBP segment.

4. The fusion protein of claim 3, wherein the linker peptide segment comprises a cleavage site for separating the target protein segment from the RBP segment.

5. The fusion protein of claim 1, wherein the wherein the target protein is operatively linked to the C-terminal end of the RBP segment.

6. The fusion protein of claim 1, wherein the target protein has a native structure and function.

7. The fusion protein of claim 1, wherein the fusion protein does not oligomerize in solution with proteins that have the same amino acid sequence of the fusion protein.

8. A method of using a recombinant expression vector to increase production of a target protein, the method comprising:

obtaining a recombinant expression vector encoding a fusion protein, the recombinant expression vector comprising an uninterrupted nucleotide sequence encoding the target protein, and a nucleotide sequence coding for a RBP segment that is at least 80% similar to amino acids 34 to 21 of SEQ ID NO:2, wherein the uninterrupted nucleotide sequence and the nucleotide sequence are operatively linked, and the fusion protein does not include a signal peptide, at least 80% identical to SEQ ID NO: 17, that targets the fusion protein to the periplasm;

introducing the recombinant expression vector into a host cell;

culturing the host cell transformed with the recombinant expression vector;

lysing the host cell to recover the fusion protein; and isolating the fusion protein.

9. The method of claim 8, wherein the recombinant expression vector further comprises a nucleic acid sequence coding for a peptidic linker comprising a proteolytic cleavage site, wherein after isolating the fusion protein, the proteolytic cleavage site is cleaved to free the target protein from the RBP segment.

10. The method of claim 9, wherein the target protein has a native structure.

11. The method of claim 8, wherein the fusion protein comprises an affinity peptide to facilitate isolating the fusion protein.

12. The method of claim 11, wherein the affinity peptide is a Histidine tail.

13. The method of claim 8, wherein the host cell is a prokaryote.

14. The method of claim 8, wherein the host cell is a eukaryote.

15. A recombinant expression vector encoding a fusion protein, the recombinant expression vector comprising an uninterrupted first nucleotide sequence coding for a target protein; and a second nucleotide sequence that a RBP amino acid sequence that is at least 80% similar to amino acids 34-211 of SEQ ID NO:2, wherein the uninterrupted first nucleotide sequence and the second nucleotide sequence are operatively linked, and the expression vector does not code for a signal peptide, at least 80% identical to SEQ ID NO: 17, that targets the fusion protein to the periplasm.

16. The recombinant expression vector of claim 15, wherein the target protein is operatively linked to the C-terminal end of the RBP segment.

17. The recombinant expression vector of claim 15, wherein the target protein is operably linked to the C-terminal end of the RBP segment.

* * * * *